United States Patent
Choi et al.

(10) Patent No.: US 7,915,428 B2
(45) Date of Patent: Mar. 29, 2011

(54) PHOTOREFRACTIVE DENDRON COMPOUND, PHOTOREFRACTIVE DENDRIMER COMPOUND, METHOD OF PREPARING THE SAME, PHOTOREFRACTIVE DEVICE USING THE SAME, AND METHOD OF MANUFACTURING THE DEVICE

(75) Inventors: Dong Hoon Choi, Seoul (KR); Min Ju Cho, Seoul (KR); Kyung Moon Jung, Jeonlanam-do (KR)

(73) Assignees: Samsung Electronics Co., Ltd. (KR); Seoul National University Industry Foundation (KR); Korea University Industrial & Academic Collaboration Foundation (KR)

( * ) Notice: Subject to any disclaimer, the term of this patent is extended or adjusted under 35 U.S.C. 154(b) by 669 days.

(21) Appl. No.: 11/868,587

(22) Filed: Oct. 8, 2007

(65) Prior Publication Data

US 2009/0223627 A1 Sep. 10, 2009

(30) Foreign Application Priority Data

Mar. 26, 2007 (KR) ........................ 10-2007-0029260

(51) Int. Cl.
*C07D 209/86* (2006.01)
*C07D 207/44* (2006.01)
(52) U.S. Cl. .................... 548/440; 548/518; 548/550
(58) Field of Classification Search .................. 548/440, 548/518, 550
See application file for complete search history.

(56) References Cited

OTHER PUBLICATIONS

Jung et al. "Photorefractive star-shaped molecular glassy materials containing tricyanopyrroline-based chromophore" Applied Physics Letters, 2007, pp. 181123-1 to 181123-3.*
Kyung Moon Jung et al., Photorefractive star-shaped molecular glassy materials containing tricyanopyrroline-based chromophore, May 3, 2007.

* cited by examiner

*Primary Examiner* — Joseph R Kosack
(74) *Attorney, Agent, or Firm* — Cantor Colburn LLP

(57) ABSTRACT

A photorefractive dendron compound, a photorefractive dendrimer compound and applications thereof, and more particularly, a photorefractive dendron compound, including a non-linear chromophore containing a tricyanopyrroline-based electron-withdrawing group and a carbazole derivative having excellent charge transport properties, a method of preparing the photorefractive dendrimer compound, a photorefractive device including the photorefractive dendrimer compound, and a method of manufacturing the photorefractive device. In the photorefractive dendrimer compound, dendron has the non-linear optical chromophore and carbazole introduced thereto to thus impart one molecule with both photoconductivity and non-linear optical properties, thereby solving conventional problems caused by poor compatibility between photoconductive material and chromophores in conventional photorefractive material. The dendrimer compound may be applied to bio-imaging techniques thanks to the use of the non-linear optical chromophore, which is sensitive to near infrared light.

10 Claims, 5 Drawing Sheets

PHOTOREFRACTIVE DENDRON COMPOUND, PHOTOREFRACTIVE DENDRIMER COMPOUND, METHOD OF PREPARING THE SAME, PHOTOREFRACTIVE DEVICE USING THE SAME, AND METHOD OF MANUFACTURING THE DEVICE

CROSS-REFERENCE TO RELATED APPLICATIONS

This non-provisional application claims priority under U.S.C. §119 from Korean Patent Application No. 10-2007-0029260, filed on Mar. 26, 2007 with the Korean Intellectual Property Office (KIPO), the entire contents of which are herein incorporated by reference.

BACKGROUND

1. Field

Exemplary embodiments relate to a photorefractive dendrimer compound and applications thereof, and more particularly, to a photorefractive dendrimer compound including a non-linear chromophore containing a tricyanopyrroline-based electron-withdrawing group and a carbazole derivative having excellent charge transport properties, a method of preparing the photorefractive dendrimer compound, a photorefractive device including the photorefractive dendrimer compound, and a method of manufacturing the photorefractive device.

2. Description of the Related Art

A photorefractive material is a material having a refractive index that varies depending on the intensity of light that is applied thereto. Generally, a photochemical reaction is used to change the refractive index depending on the intensity of light. Such a photochemical reaction is irreversible, and is thus suitable for use as an information storage medium, but is unsuitable for use as an information processing medium.

Therefore, there is a need for a material the refractive index of which may be reversibly controlled depending on the intensity of light. To this end, not a photochemical reaction but a photophysical phenomenon should be used. The photorefractive material having photocurrent and electro-optcal phenomena is a typical material able to reversibly control the refractive index. When the photorefractve material is exposed to light, electric charges are generated therein in proportion to the intensity of light due to the photocurrent thereof. The electric charges thus generated are moved by diffusion or drift. As such, the difference in the concentration of the electric charges within the material occurs to thus form an internal space-charge field. Further, because this material may represent an electro-optical phenomenon, the refractive index of the material changes in proportion to the magnitude of the internal space-charge field. That is, the refractive index of the material is reversibly changed in proportion to the intensity of light, which is referred to as a "photorefractive phenomenon".

The photorefractive phenomenon was first discovered using $LiNbO_3$ in 1966 by Ashkin, who considered the phenomenon to be nothing more than damage to the material caused by a laser. However, after one year, Chen in the Bell Institute revealed that the phenomenon is caused not by laser damage but by a fanning phenomenon based on the reversible refractive index change. Accordingly, the photorefractive phenomenon came to be recognized as a new optical phenomenon. Although photorefractive material using an inorganic material has been proven to be applicable as various optical materials, it has not yet been commercialized because the above material is difficult to process and expensive inorganic material is used. On the other hand, the photorefractive phenomenon of an organic material was first discovered from organic crystalline COANP (2-cyclooctylamino-5-nitropyridine) including TCNQ (7,7,8,8-tetracyclo-quinodimethane) in 1990, and was observed using a crosslinked epoxy-based non-linear polymer material containing DHE (diethylamino-benzaldehyde diphenylhydrazone) as a charge transport molecule the following year. Organic material is receiving attention because it is relatively easy to prepare, is inexpensive, thus enabling mass production, and may have easily controllable chemical components and structures, thus making it suitable for various applications. However, the organic photorefractve material still has many problems, including a low response speed, high electric field for application, and poor durability, upon application to real-time information processing.

Recent research into photorefraction is focused on organic photorefracton, which is reaction in response to near infrared light, and is used in biological applications. The biotissue has high light transmittance at wavelengths of 700~900 nm. When near infrared light is radiated onto the tissue, not only light reflected from the surface of the issue but also various scattering rays are simultaneously emitted, depending on the depth of penetration of light into the tissue. In this case, when the scattering rays are selectively sorted, depending on the depth, and are then imaged, an image of the tissue section may be realized from two-dimensional images taken at different depths. This is the bio-imaging technique.

W. E. Moerner reported a remarkable gain coefficient of 370 $cm^{-1}$ under near infrared light (830 nm) using a mixture including two types of organic glass (Appl. Phys. Lett., Vol 82, pp. 3602 (2003)). However, the device manufactured using the low-molecular-weight material mixture is known to have poor durability due to crystallization, and furthermore, has a very low response speed, undesirably decreasing the applicability thereof as a device for near infrared transmission holograms. Therefore, although it is important to have a high gain coefficient, a material having superior device stability and a high response speed is required for actual application to hologram devices.

SUMMARY

Leading to exemplary embodiments, intensive and thorough research into photorefractive materials having superior device stability and a high response speed to thus solve the problems encountered in the related art, resulted in the finding that the crystallization of chromophores may be prevented through site-isolation, thereby manufacturing a photorefractive device having high stability, unlike general organic glass materials.

Exemplary embodiments provide a photorefractive dendron compound, a photorefractive dendrimer compound and a method of preparing the same. Exemplary embodiments provide a photorefractive device including the photorefractive dendrimer compound and a method of manufacturing the same.

According to exemplary embodiments, there is provided a photorefractive dendron compound represented by Formula 1 or 5, including a non-linear chromophore containing a tricyanopyrroline-based electron-withdrawing group and a carbazole derivative having excellent charge transport properties.

According to exemplary embodiments, there is provided a method of preparing the photorefractive dendron compound and the photorefractive dendrimer compound.

According to exemplary embodiments, there is provided a photorefractive device including the photorefractive dendrimer compound.

According to exemplary embodiments, there is provided a method of manufacturing the photorefractive device.

BRIEF DESCRIPTION OF THE DRAWINGS

Exemplary embodiments will be more clearly understood from the following detailed description taken in conjunction with the accompanying drawings.

FIG. 1 is a schematic view illustrating the process of manufacturing a device for evaluating the optical properties of an optical dendrimer compound according to exemplary embodiments;

FIG. 2 is a graph illustrating the glass transition temperature of the optical dendrimer compounds according to exemplary embodiments;

FIG. 3 is a graph illustrating the UV-Vis absorbance of the compounds in a film form, according to exemplary embodiments;

FIG. 4 is a graph illustrating the birefringence measured using the devices of the optical dendrimer compounds according to exemplary embodiments; and FIG. 5 is a graph illustrating the gain coefficient depending on the applied voltage using the devices of the optical dendrimer compounds according to exemplary embodiments.

Figure 1:
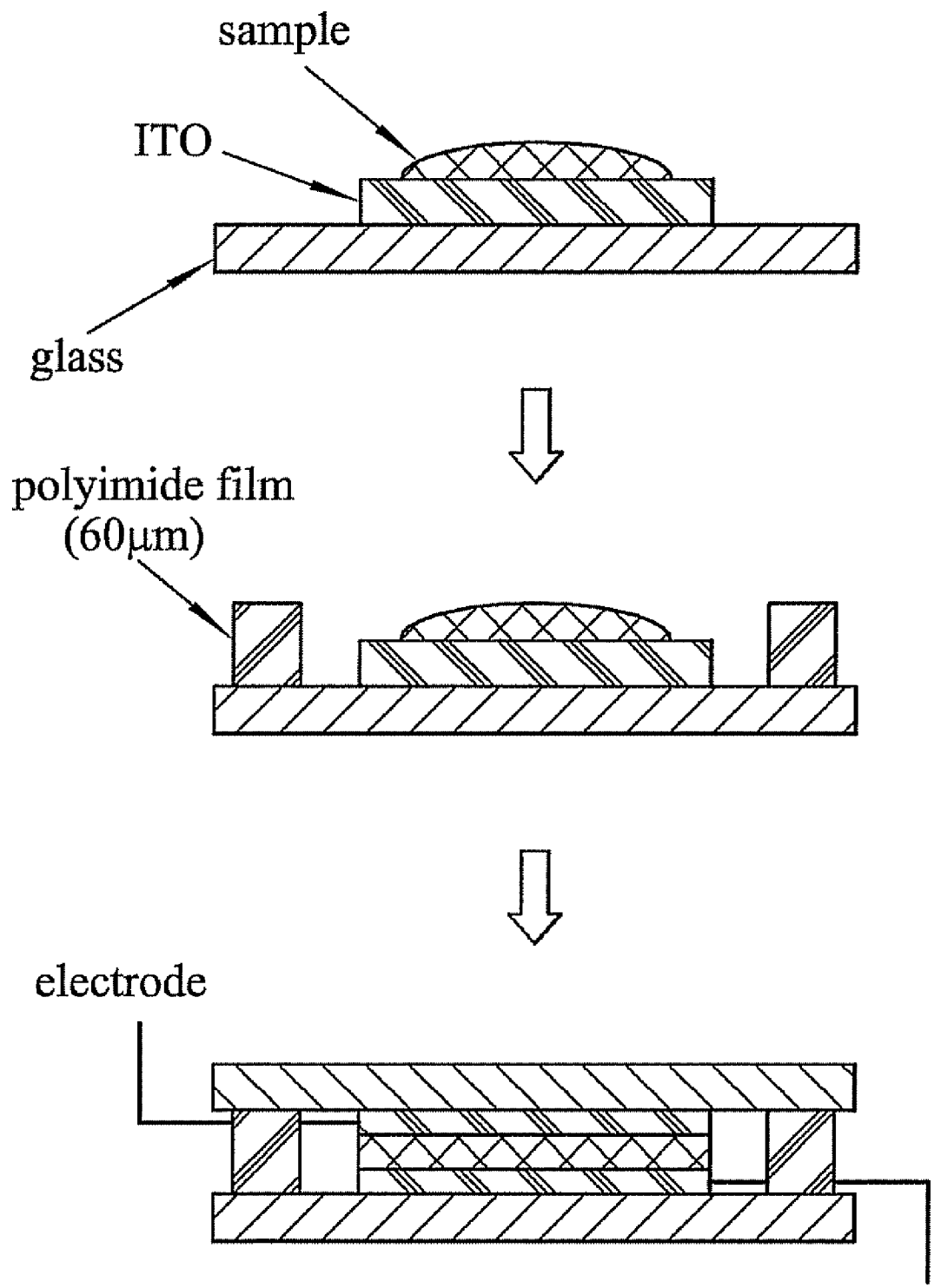
FIGS. 1-5 represent non-limiting, exemplary embodiments described herein.

It should be noted that these figures are intended to illustrate the general characteristics of methods, structures and/or materials utilized in certain exemplary embodiments and to supplement the written description provided below. These drawings are not, however, to scale, and may not precisely reflect the precise structural or performance characteristics of any given embodiment, and should not be interpreted as defining or limiting the range of values or properties encompassed by exemplary embodiments. In particular, the relative thicknesses and positioning of molecules, layers, regions and/or structural elements may be reduced or exaggerated for clarity. The use of similar or identical reference numbers in the various drawings is intended to indicate the presence of a similar or identical element or feature.

DESCRIPTION OF THE PREFERRED EMBODIMENTS

Hereinafter, a detailed description will be given of exemplary embodiments.

Exemplary embodiments provide a photorefractive dendron compound represented by Formula 1 or Formula 5 below, which includes a non-linear chromophore containing a tricyanopyrroline-based electron-withdrawing group and a carbazole derivative having excellent charge transport properties:

Formula 1

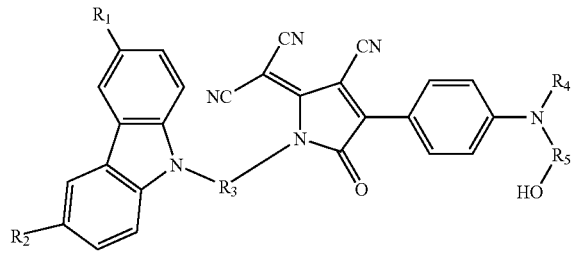

wherein $R_1$, $R_2$ and $R_4$ are each $C_{1-20}$ branched or unbranched alkyl group, and $R_3$ and $R_5$ are each $C_{1-20}$ alkylene group.

Formula 5

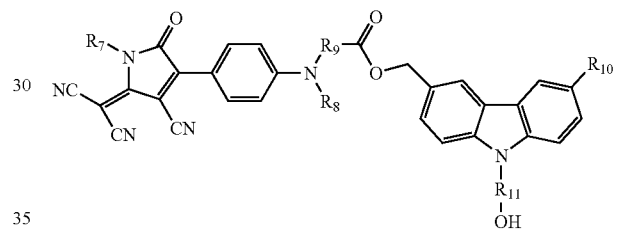

wherein $R_7$, $R_8$ and $R_{10}$ are each $C_{1-20}$ branched or unbranched alkyl group, and $R_9$ and $R_{11}$, are each $C_{1-20}$ alkylene group.

A

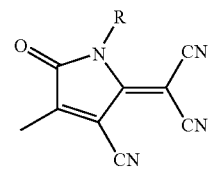

group of formula 1 or 4 is a strong electron-withdrawing dye, TCP (3-methyl-4-cyano-5-dicyanomethylene-2-oxo-3-pyrroline). Another strong electron-withdrawing dye is TCF (2-dicyanomethylene-3-cyano-4,5,5-trimethyl-2,5-dihydrofuran).

In the photorefractive dendron compound of exemplary embodiments, said $R_1$, $R_2$, $R_3$, $R_4$, $R_5$, $R_7$, $R_8$, $R_9$, $R_{10}$ and $R_{11}$, may be an alkyl group or alkylene group. The alkyl chain may consist of 1 to 20 carbons to thus change the glass transition temperature thereof.

Further, in the photorefractive dendron compound of exemplary embodiments, the dendron compound may be a compound represented by Formula 2 or Formula 6 below.

Formula 2
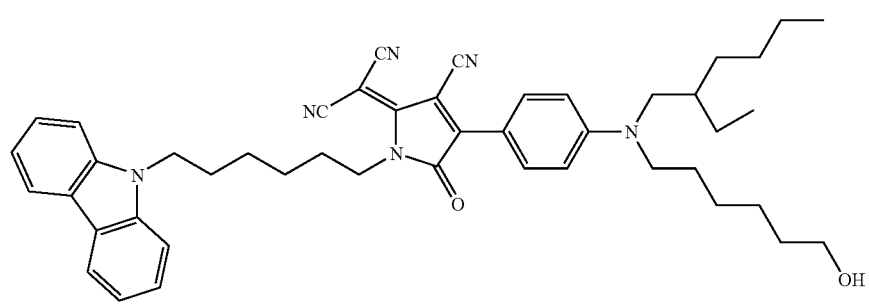
Formula 6
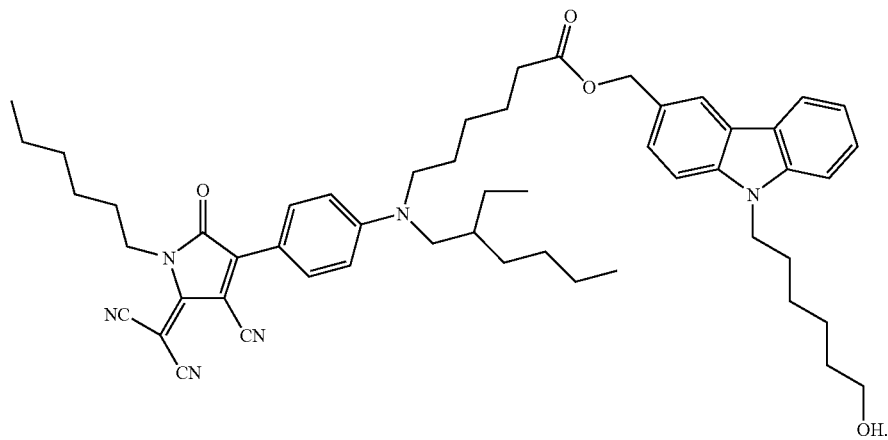
Furthermore, in a photorefractive dendrimer compound of exemplary embodiments, a dendrimer compound may be a compound represented by Formula 3 or Formula 7 below.
Formula 3
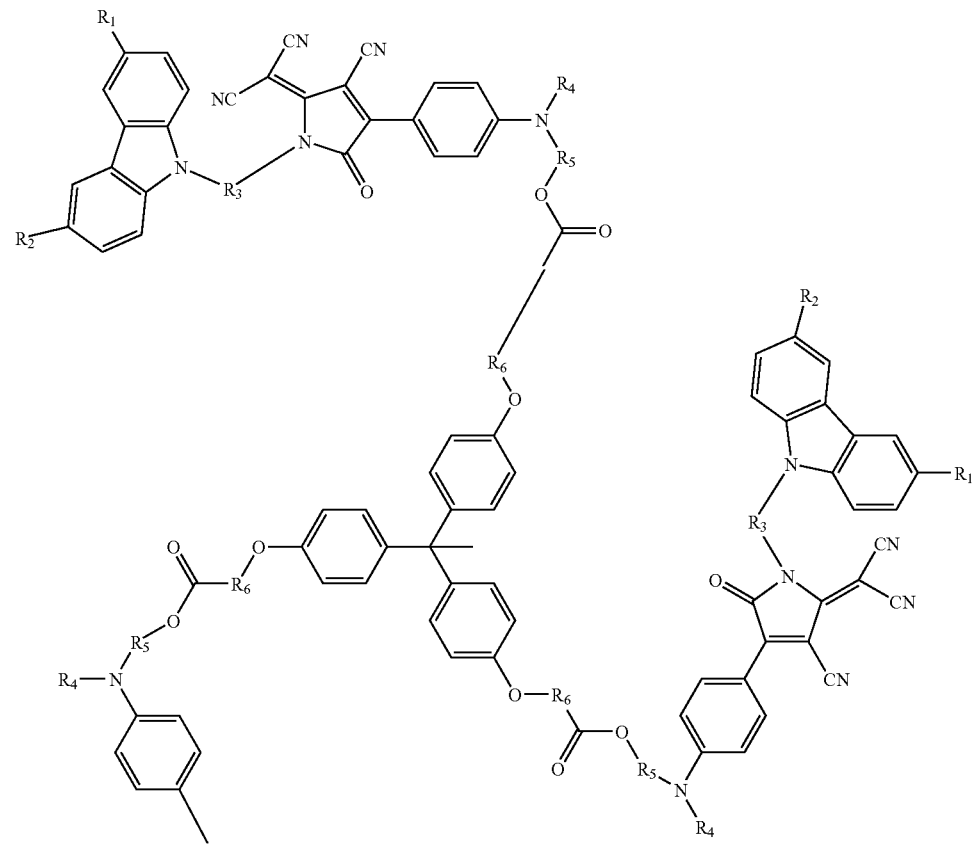

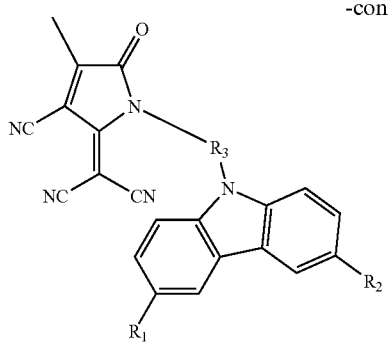
wherein $R_1$, $R_2$ and $R_4$ are each $C_{1-20}$ branched or unbranched alkyl group, and $R_3$, $R_5$ and $R_6$ are each $C_{1-20}$ alkylene group.
Formula 7
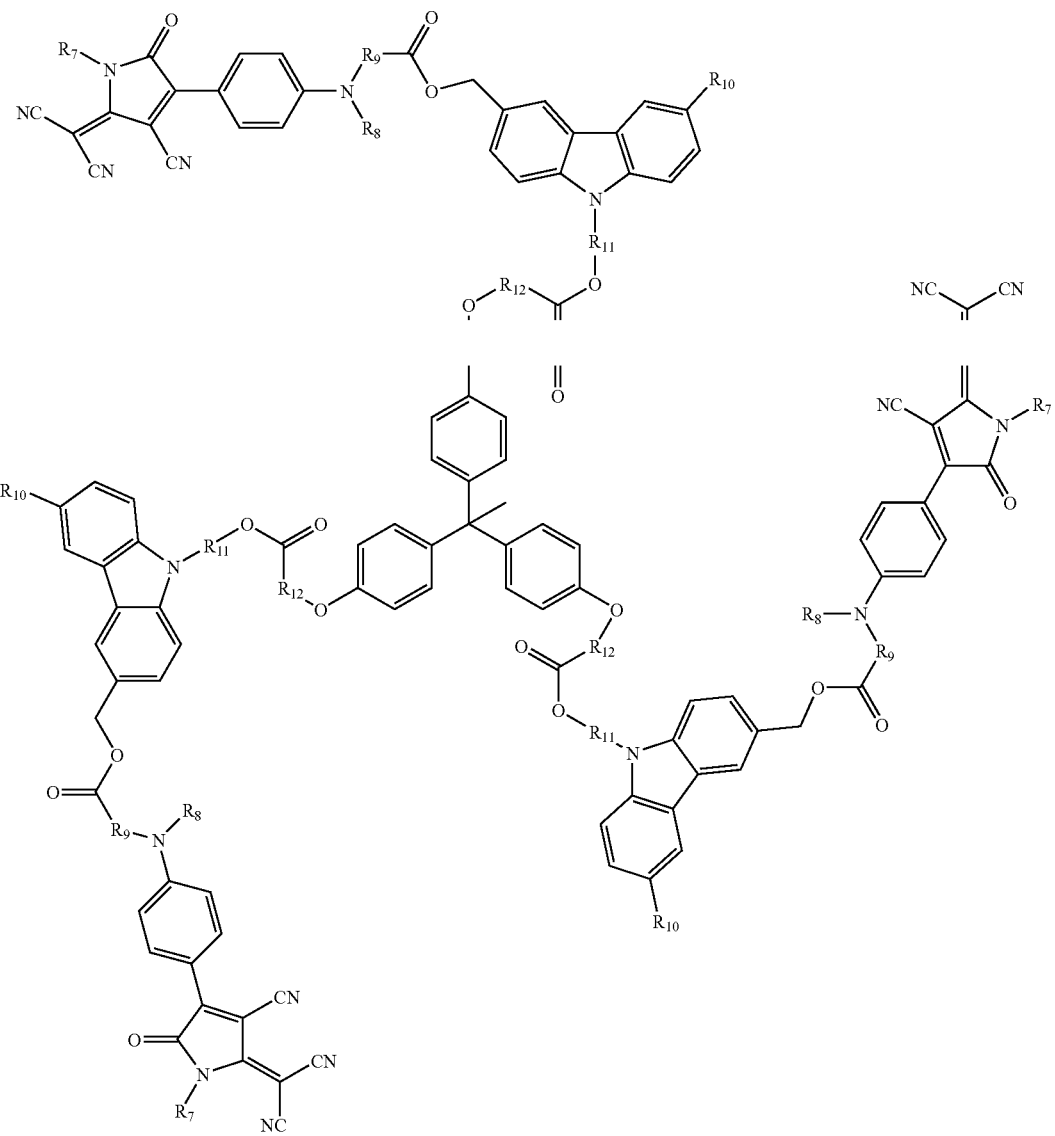

wherein $R_7$, $R_8$ and $R_{10}$ are each $C_{1-20}$ branched or unbranched alkyl group, and $R_9$, $R_{11}$ and $R_{12}$ are each $C_{1-20}$ alkylene group.
Furthermore, in the photorefractive dendrimer compound of exemplary embodiments, the dendrimer compound may be a compound represented by Formula 4 or Formula 8 below.
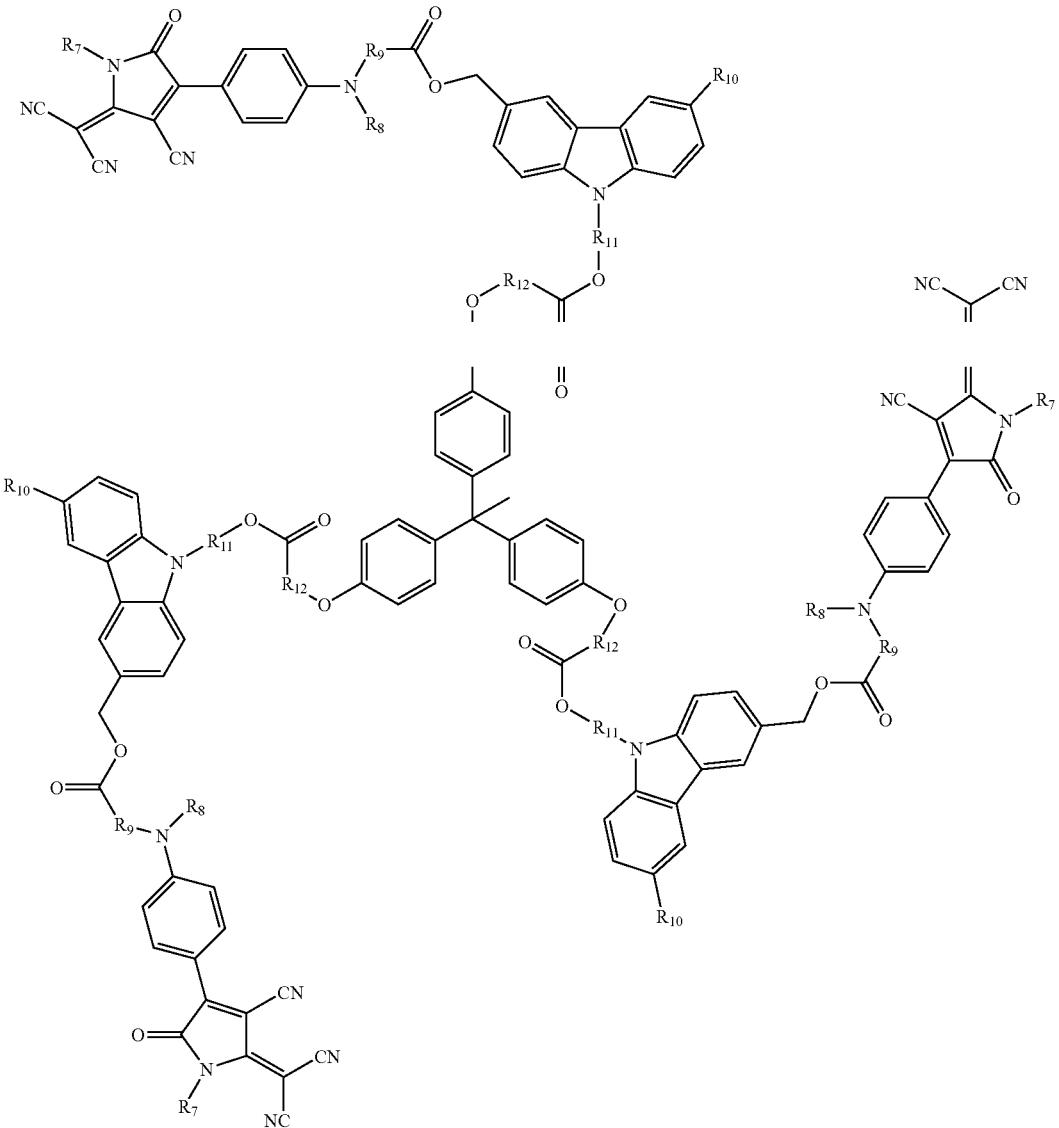
Formula 4
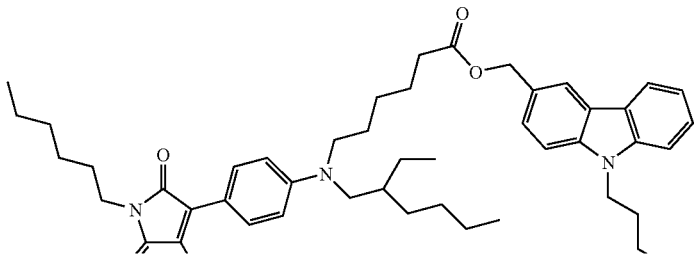
Formula 8

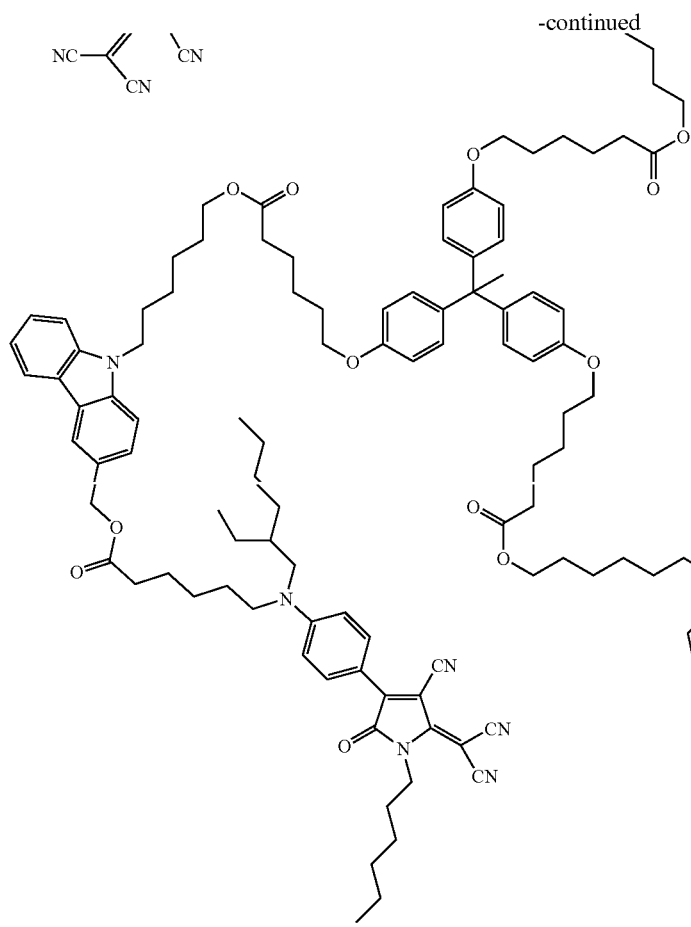
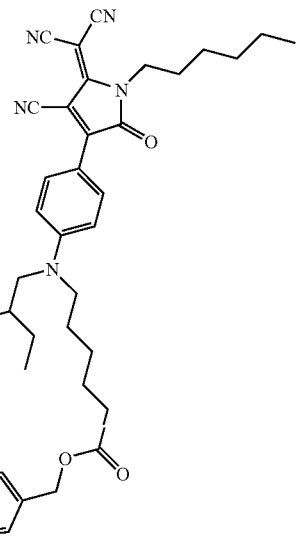

In exemplary embodiments, the structure of the photorefractive dendrimer compound is characterized in that the carbazole derivative is located at the outer part of the dendrimer to thus improve charge transport properties, and in addition, the functional chromophores are introduced to the outer parts of the dendrimer to thereby decrease electrostatic interactions between chromophoric macromolecules. This compound is designed such that both photoconductivity and secondary non-linear optical properties are simultaneously realized in one compound structure. Such structural characteristics may realize site-isolation, thereby making it possible to effectively solve conventional problems in which the chromophores are crystallized due to interactions therebetween, that is, conventional photorefractive material undergoes phase separation and crystallization to undesirably cause poor durability. Further, the glass transition temperature, which has a direct influence on the photorefractive index, may be effectively adjusted by changing the length of the alkyl chain, which has 1 to 20 carbons. Thereby, a near infrared light sensitive photorefractive material having outstanding stability as a photorefractive device may be provided.

In particular, the photorefractive dendrimer compound includes a non-linear chromophore and thus exhibits high sensitivity to infrared light at 830 nm and high performance. Hence, photorefraction using the dendrimer compound of example embodiments may be effectively applied to biological samples, for example, human bodies, having high long-wavelength light transmittance.

In addition, exemplary embodiments provide a method of preparing the photorefractive dendron compound.

In the method of preparing the photorefractive dendron compound, 2-(1-(6(9H-carbazol-9-yl)hexyl)-3-cyano-4-(4-((2-ethylhexyl)(6 hydroxyhexyl)amino)phenyl)-5-oxo-1H-pyrrol-2(5H)-ylidene)malononitrile, represented by Formula 2, may be synthesized through Reaction 4 below.

Reaction 4

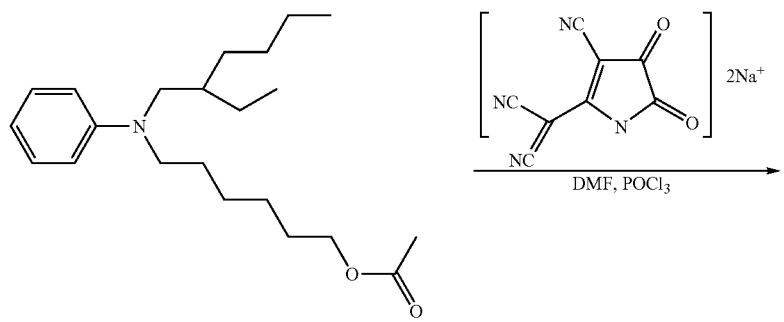

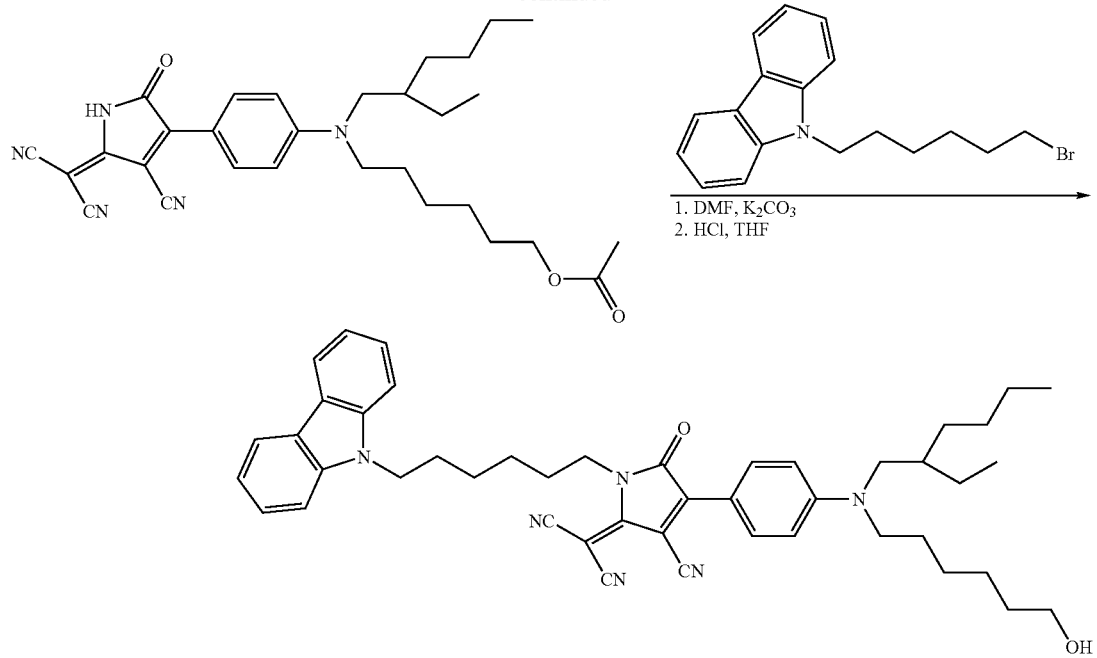
Further, in the method of preparing the photorefractive dendron compound, (9-(6-hydrohexyl)-9H-carbazol-3-yl)methyl6-((4-(4-cyano-5-(dicyanomethylene)-1-hexyl-2-oxo-2,5-dihydro-1H-pyrrol-3-yl)phenyl)(2-ethylhexyl)amino)hexanoate, represented by Formula 6, may be synthesized through Reaction 5 below.
Reaction 5
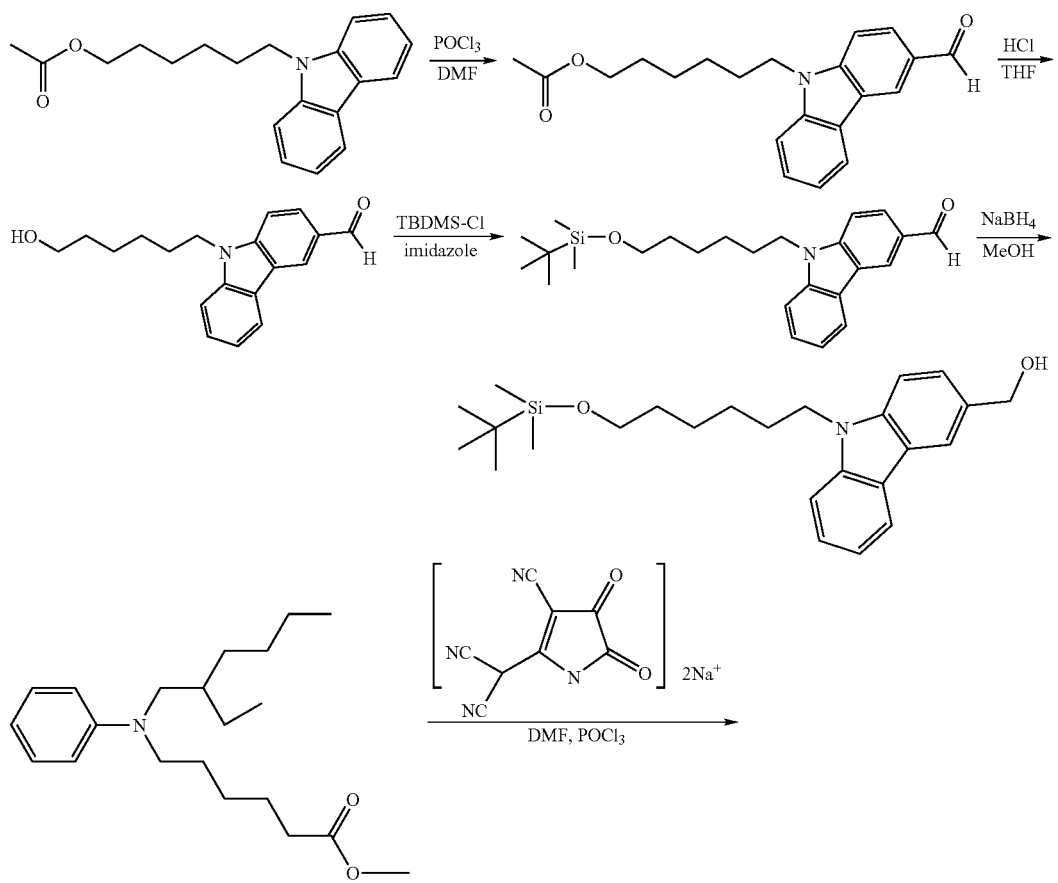

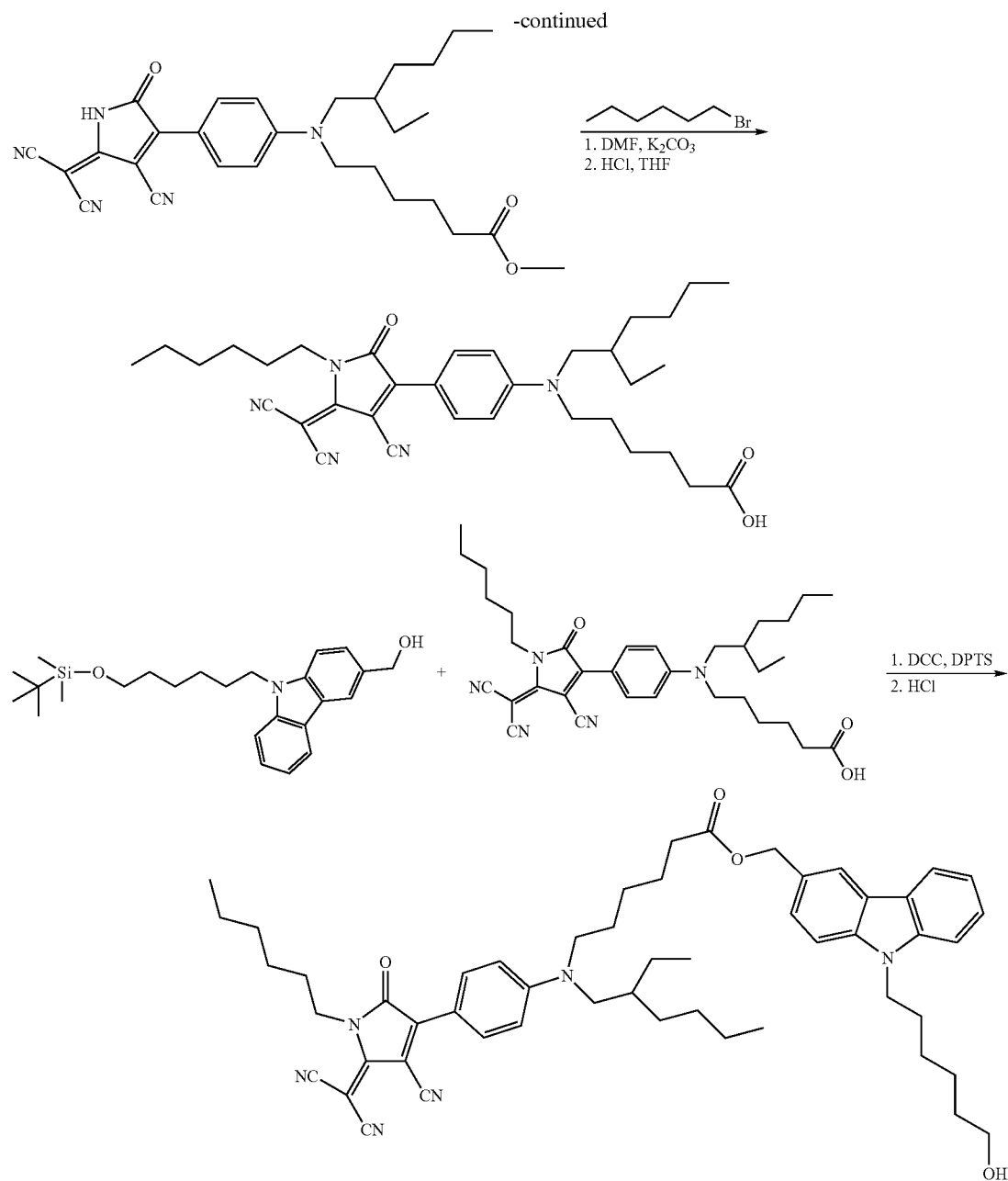
Further, in the method of preparing the photorefractive dendrimer compound, the photorefractive dendrimer 1 or the photorefractive dendrimer 2, represented by Formula 4 or Formula 8, may be synthesized through Reaction 4 or Reaction 5, and additionally, through Reaction 3 below.
Reaction 3
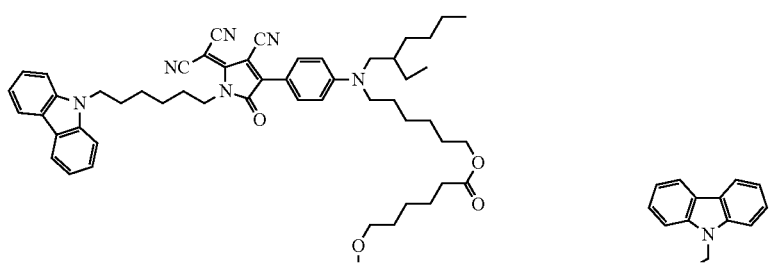

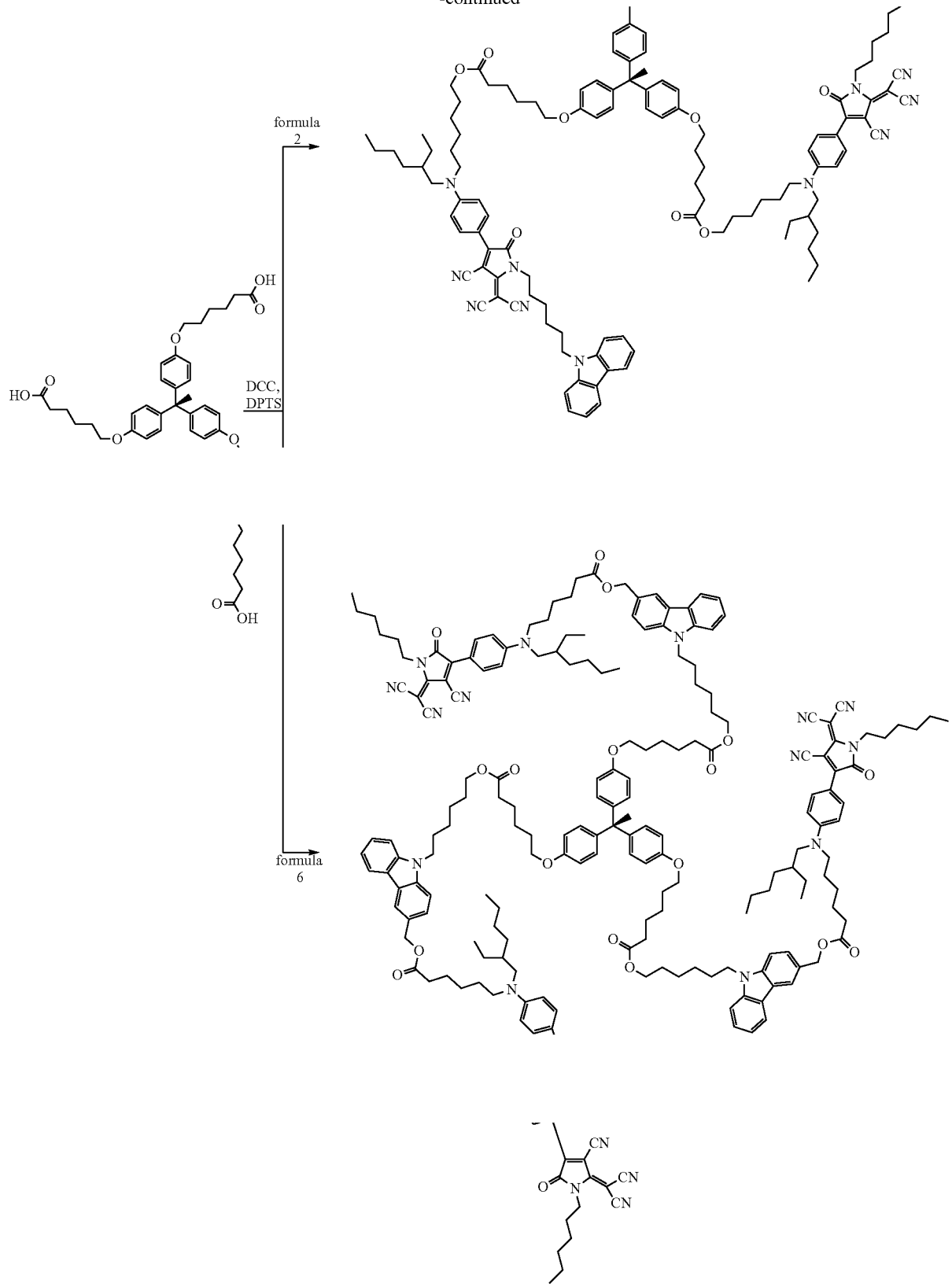
According to exemplary embodiments, the organic electroluminescent dendrons and dendrimers represented by Formulas 1 to 8 may be synthesized through the preparation process of Reactions 1, 2 and 3 below.

Reaction 1

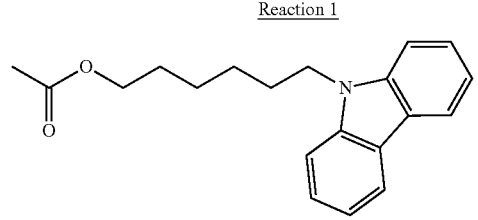

1

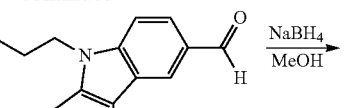

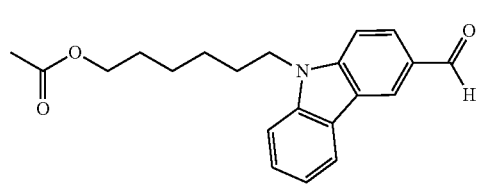

2

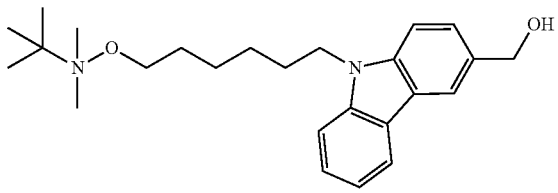

4

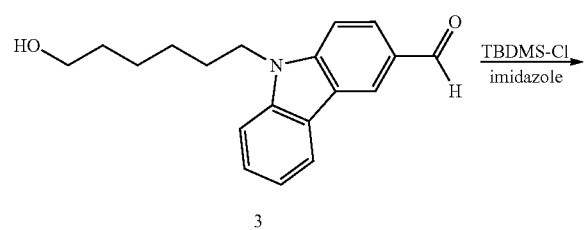

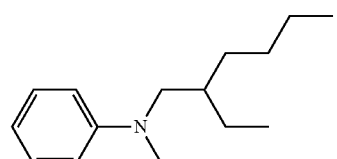

3

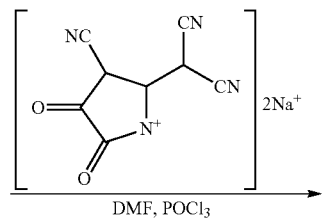

5

In Reaction 1, a reactant reacts with 1,2-dichloroethane at 0° C. to thus prepare a precursor 2, which is then further reacted in the presence of 10% HCl, affording a precursor 3. The reaction is progressed through reflux. Then, 9-(6-hydroxyhexyl)-9H-carbazole-3-carbaldehyde, dichloromethane, tert-butyldimethylsilyl chloride, and imidazole are reacted together, thus producing 4 (9-(6-(tert-butyldimethylsilyloxy)hexyl)-9H-carbazole-3-carbaldehyde) as a precursor. Then, the precursor 4 is dissolved in sodium borohydride and methanol to thus allow the obtained solution to react, yielding 5 ((9-(6-(tert-butyldimethylsilyloxy)hexyl)-9H-carbazol-3-yl)methanol as a precursor.

Reaction 2

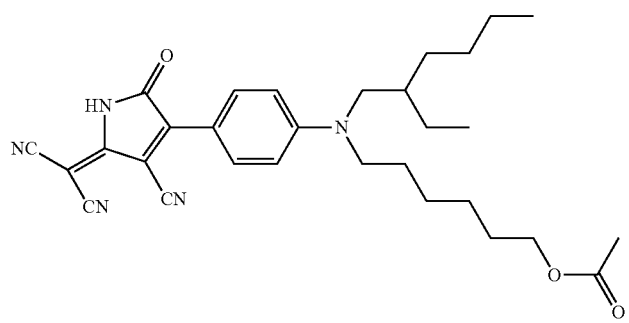

6

7

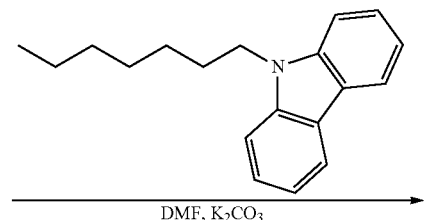

-continued
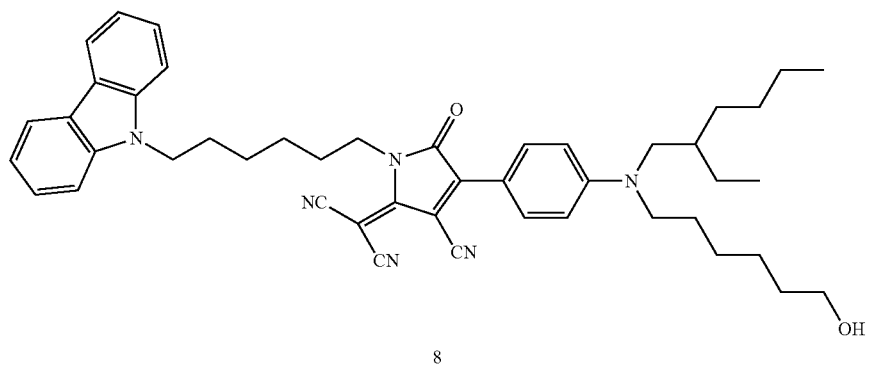
8
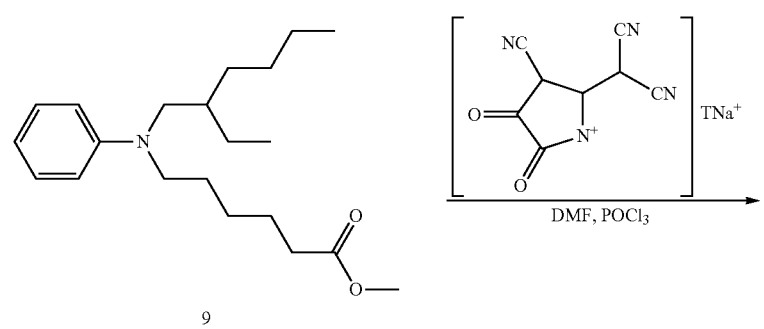
9
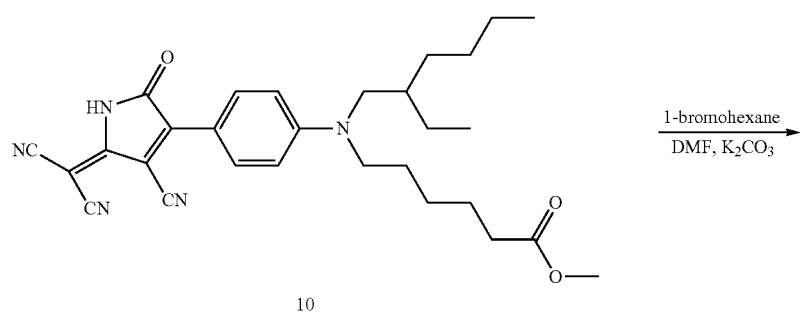
10
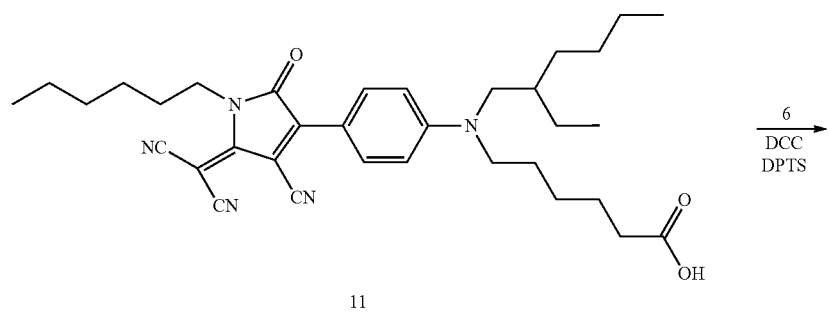
11

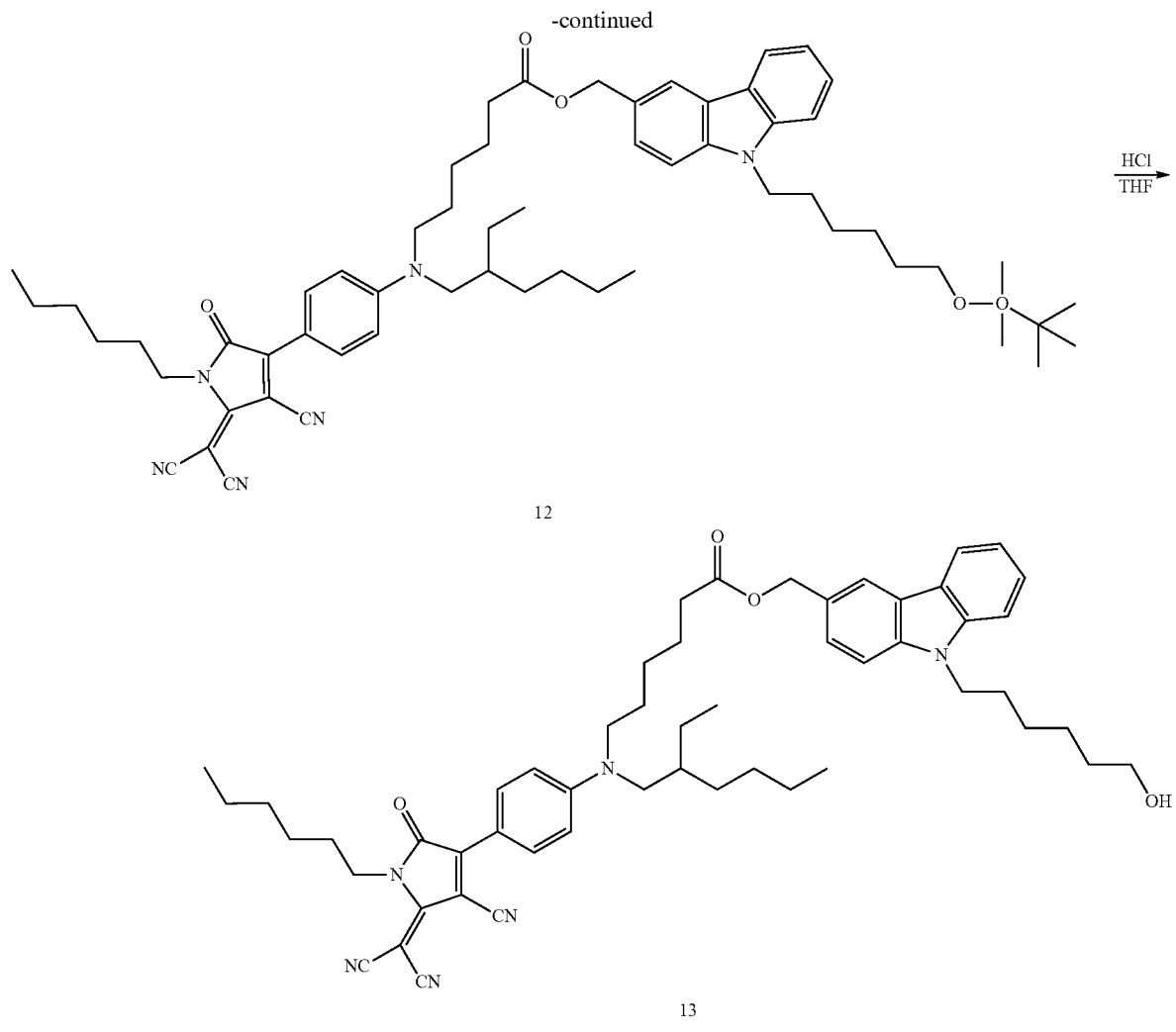

12

13

In Reaction 2, a precursor 6 (6-((2-ethylhexyl)(phenyl)amino)hexyl acetate) is prepared by reacting 6-((2-ethylhexyl)(phenyl)amino)hexan-1-ol, acetic anhydride and pyridine. The precursor 6, dimethylformamide, acetic anhydride, and 4-cyano-5-dicyanomethylene-3-hydroxy-2-oxo-3-pyrroline disodium salt are reacted to thus prepare a precursor 7 (6-((4-cyano-5-(dicyanomethylene)-2-oxo-2,5-dihydro-1H-pyrrol-3-yl)phenyl)(2-ethylhexy)amino)hexyl acetate). Thereafter, 6-((2-ethylhexyl)(phenyl)amino)hexyl acetate, sodium carbonate, dimethylformamide, and 9-(6-bromohexyl)-9H-carbazole are reacted to thus prepare 6-((4-(6-(9H-carbazol-9-yl)hexyl-4-cyano-5-(dicyanomethyl)-2-oxo-2,5-dihydro-1H-pyrrol-3-yl)phenyl(2-ethylhexyl)amino)hexyl acetate, which is then mixed with tetrahydrofuran and hydrochloric acid, thus obtaining a compound 8 (2-(1-(6-(9H-carbazol-9-yl)hexyl)-3-cyano-4(4-((2-ethylhexyl)(6-hydroxyhexyl)amino)phenyl)-5-oxo-1H-pyrrol-2(5H)-ylidene)malononitrile). The compound 8 is the dendron compound represented by Formula 2.

A precursor 9 (methyl 6-((2-ethylhexyl)(phenyl)amino) hexanoate) is obtained by reacting methyl 6-(phenylamino) hexanoate, potassium carbonate, dimethylformamide, and 3-(bromomethyl)heptane. Then, 6-((2-ethylhexyl)(phenyl)amino)hexyl acetate, dimethylformamide, acetic anhydride, 4-cyano-5-dicyanomethylene-3-hydroxy-2-oxo-3-pyrroline disodium salt, and POCl₃ are reacted to thus prepare a precursor 10 (methyl6-((4-(4-cyano-5-(dicyanomethyene)-2-oxo-2,5-dihydro-1H-pyrrol-3-yl)phenyl)(2-ethylhexyl) amino) hexanoate). Then, methyl 6-((4-(4-cyano-5-(dicyanomethylene)-2-oxo-2,5-dihydro-1H-pyrrol-3-yl) phenyl)(2-ethylhexyl)amino) hexanoate, potassium carbonate, dimethylformamide, and 1-bromohexane are reacted to thus produce methyl 6-((4-(4-cyano-5-(dicyanomethyene)-1-hexyl-2-oxo-2,5-dihydro-1H-pyrrol-3-yl)phenyl)(2-ethylhexyl)amino)hexanoate, which is then reacted with tetrahydrofuran and hydrochloric acid, yielding a precursor 11 (6-((4-(4-cyano-5-(dicyanomethylene)-1-hexyl-2-oxo-2,5-dihydro-1H-pyrrol-3-yl)phenyl)(2-ethylhexyl) amino) hexanoic acid). Then, 6-((2-ethylhexyl)(phenyl) amino)hexyl acetate, 6-((4(4-cyano-5-(dicyanomethylene)-1-hexyl-2-oxo-2,5-dihydro-1H-pyrrol)-3-yl)phenyl)(2-ethylhexyl)amino)hexanoic acid, DPTS, dicyclohexyl carbodiimide, and dichloromethyl are reacted together, thus obtaining a precursor 12 ((9-(6-(tert-butyldimethylsilyloxy) hexyl)-9H-carbazol-3-yl)methyl 6-((4-(4-cyano-5-(dicyanomethylene)-1-hexyl-2-oxo-2,5-dihydro-1H-pyrrol-3-yl) phenyl)(2-ethylhexyl)amino)hexanoate). Then, (9-(6-(tert-butyldimethylsilyloxy)hexyl)-9H-carbazol-3-yl)methyl 6-((4-(4-cyano-5-(dicyanomethylene)-1-hexyl-2-oxo-2,5-dihydro-1H-pyrrol-3-yl)phenyl)(2-ethylhexyl)amino)hexanoate, tetrahydrofuran, and hydrochloric acid are reacted together, yielding a compound 13 ((9-(6-hydrohexyl)-9H-carbazol-3-yl)methyl6-((4-(4-cyano-5-(dicyanomethylene)-1-hexyl-2-oxo-2,5-dihydro-1H-pyrrol-3-yl)phenyl)(2-ethyl-hexyl)amino)hexanoate). The compound 13 is the dendron compound represented by Formula 6 according to exemplary embodiments.
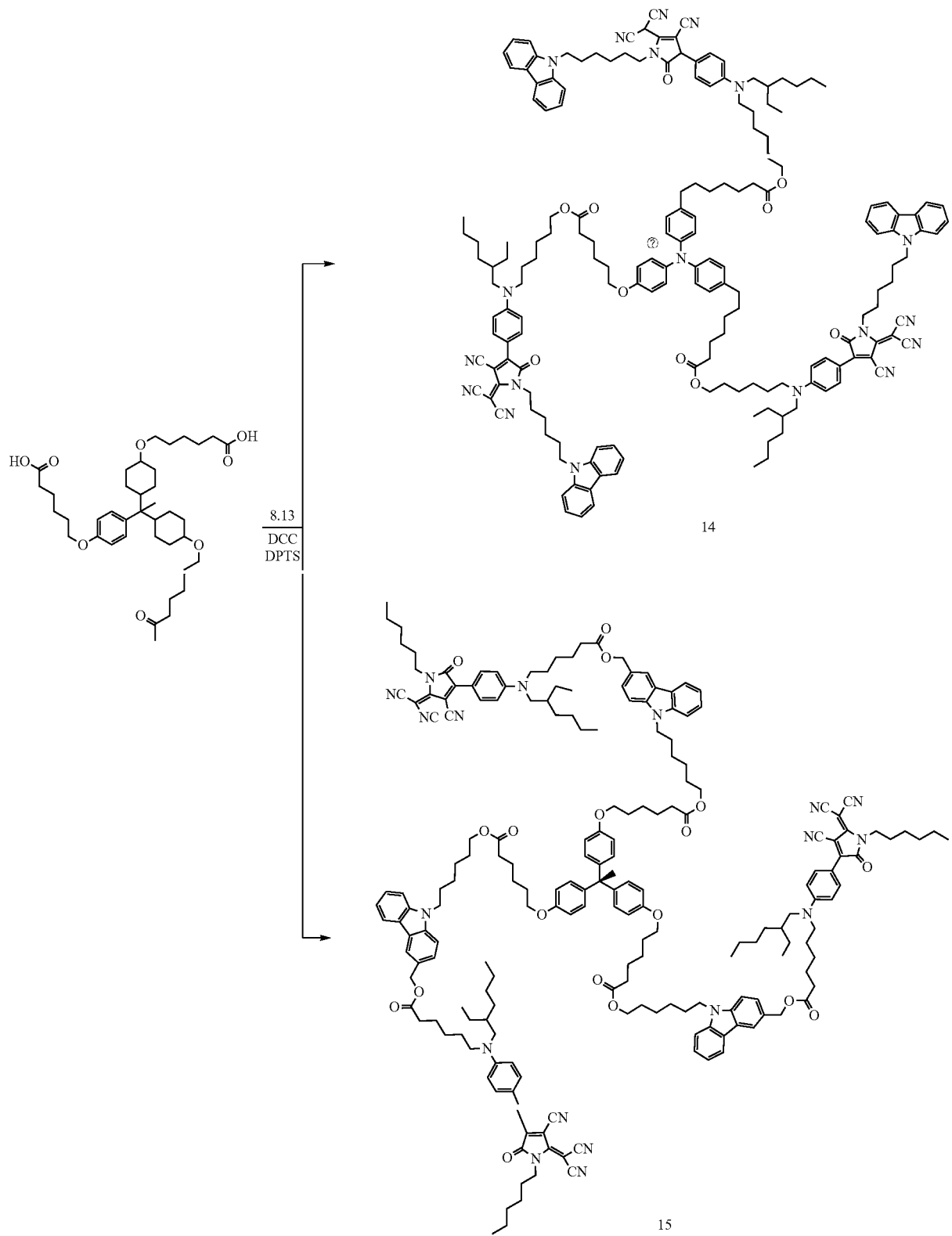

The dendrimer represented by the compound 14 and the compound 15 may be synthesized through the preparation process of the above reactions. Specifically, the photorefractive dendrimer 1 (compound 14) is prepared by reacting 2-(1-(6-(9H-carbazol-9-yl)hexyl)-3-cyano-4-(4-((2-ethylhexyl)(6-hydroxyhexyl)amino)phenyl)-5-oxo-1H-pyrrol-2(5H)-ylidene) malononitrile, 6,6',6''-(4,4',4''-(ethane-1,1,1-trinyl) tris(4,1-phenylene))tris (oxy)trihexanoic acid, DPTS, and dicyclohexylcarbodiimide. In addition, the photorefractive dendrimer 2 (compound 15) is prepared by reacting (9-(6-hydrohexyl)-9H-carbazol-3-yl)methyl6-((4-(4-cyano-5-(dicyanomethylene)-1-hexyl-2-oxo-2,5-dihydro-1H-pyrrol-3-yl)phenyl)(2-ethylhexyl)amino)hexanoate, 6,6',6''-(4,4',4''-(ethane-1,1,1-trinyl)tris(4,1-phenylene))tris (oxy) trihexanoic acid, DPTS, and dicyclohexylcarbodiimide.

In Reaction 3, the compound 14 is the dendrimer compound represented by Formula 4 according to the exemplary embodiments, and the compound 15 is the dendrimer compound represented by Formula 8 according to the exemplary embodiments.

In addition, the exemplary embodiments provide a photorefractve device including the photorefractve dendrimer compound.

Figure 2:
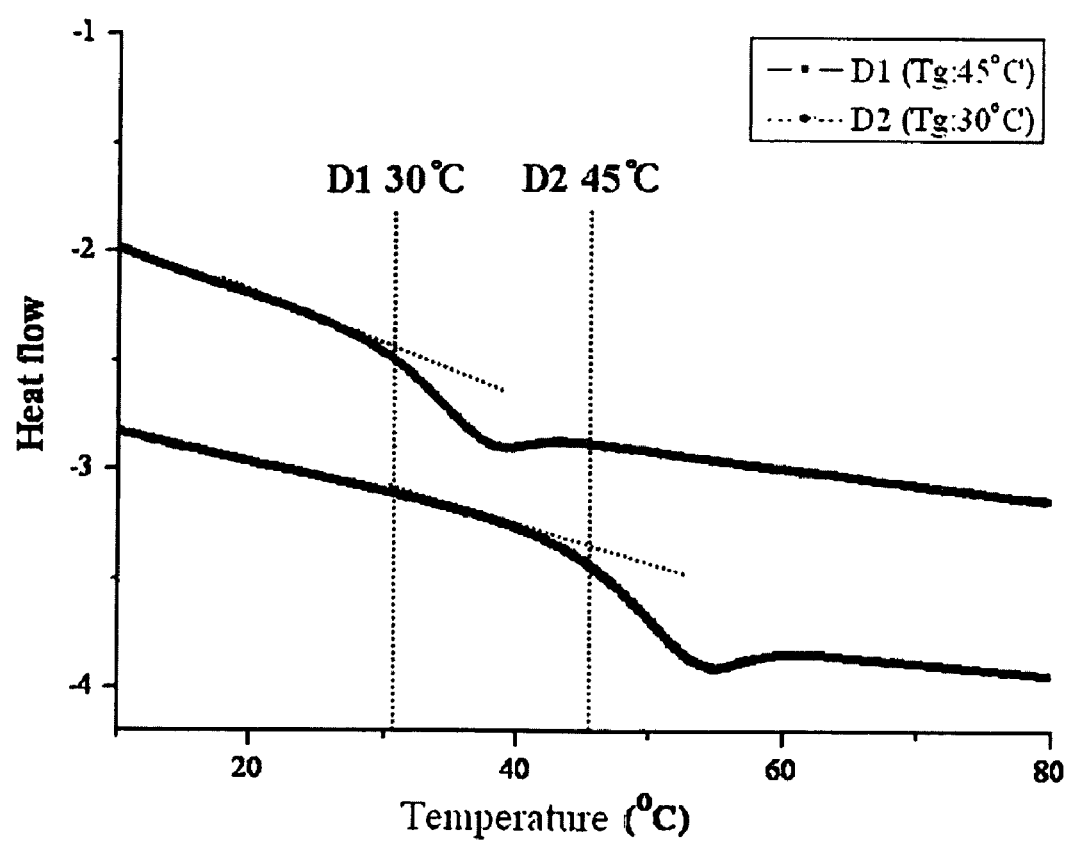

As the results of measurement of the voltage-gain coefficient of the device, which represents the glass transition temperature of the optical dendrimer compound of the exemplary embodiments, the D1 and D2 materials are found to have glass transition temperatures of 30° C. and 45° C., respectively, which are close to room temperature. This is because the non-linear chromophores, which are structural components of the dendrimer compound, may be easily oriented in the direction of the electric field (FIG. 2).

Figure 3:
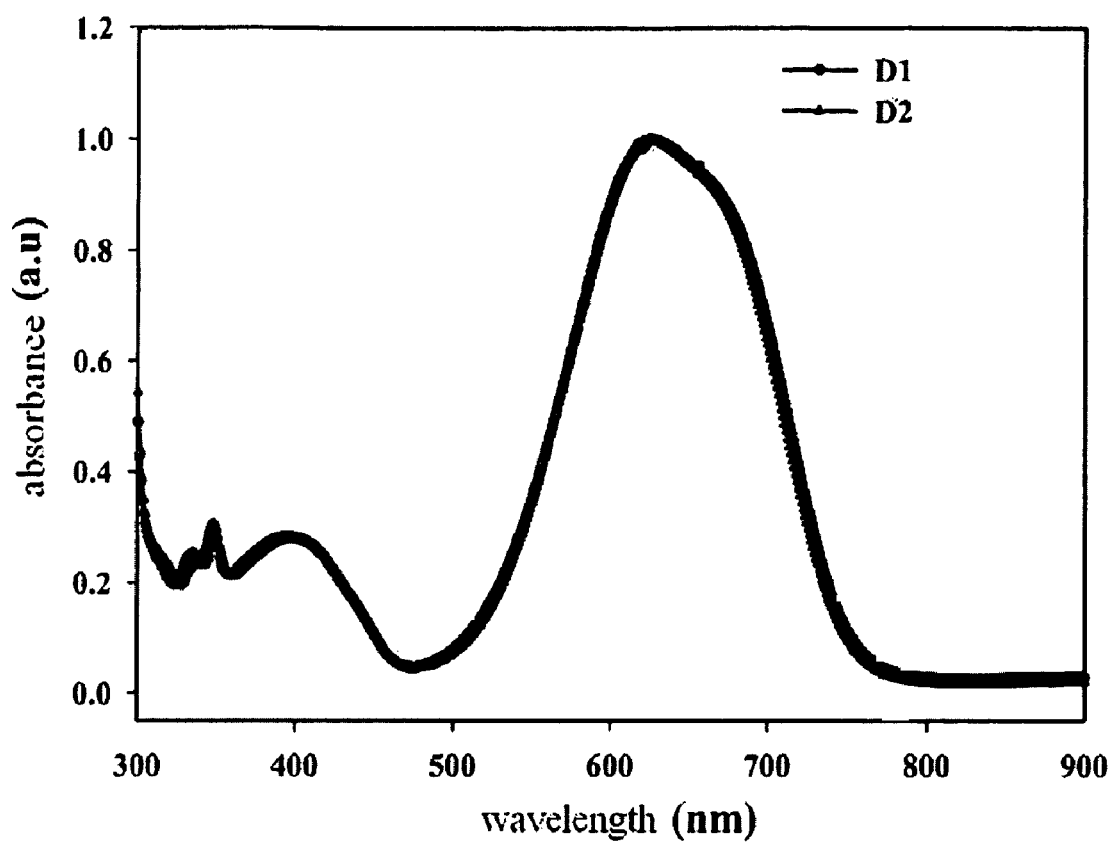

As the results of measurement of the UV-Vis spectra of D1 and D2 in the form of a film, the absorption spectra of the D1 and D2 materials have almost the same shape. This is because the two materials have the same non-linear chromophore and carbazole, in which the maximum absorption wavelength is formed at 625 nm by the non-linear chromophore and at 350 nm by the carbazole (FIG. 3).

Figure 4:
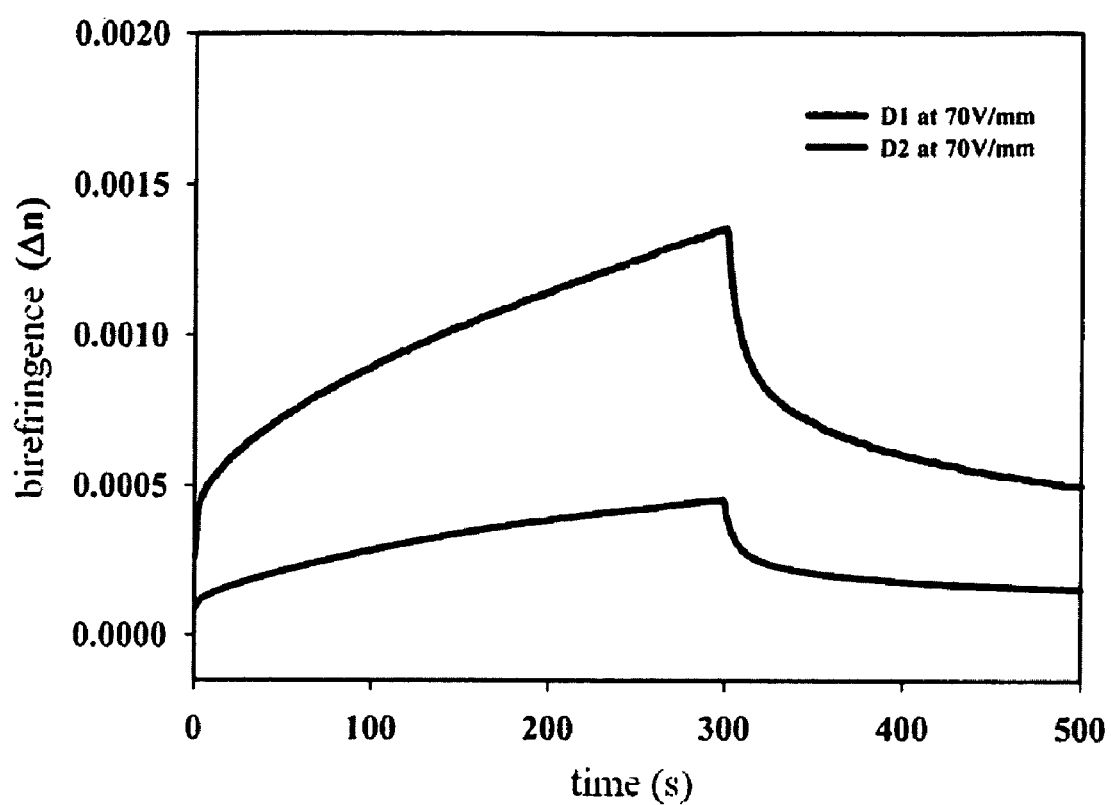

As the results of measurement of birefringence of D1 and D2 using the devices of the optical dendrimer compounds, D2, in which the non-linear chromophores are located at the outer parts thereof, may be more easily oriented, and thus has higher birefringence (FIG. 4).

Figure 5:
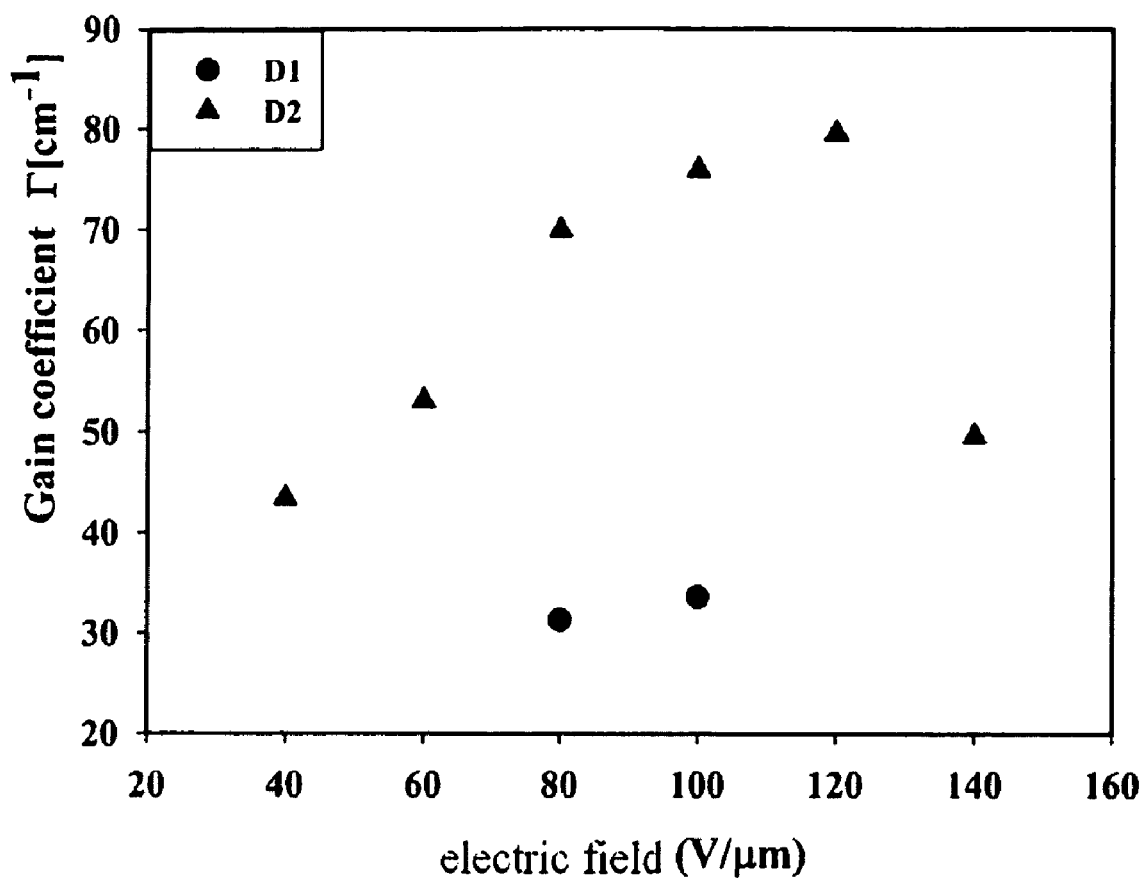

A TBC (Two Beam Coupling) test is very important in the photorefractive material. As the results of measurement of gain coefficient depending on the applied voltage using the devices of the optical dendrimer compounds, D1 and D2 are found to have similar photoconductivity due to the addition of the same amount of carbazole. However, in the TBC test, D2 has better material orientation, which means that much more energy transfer may be realized by D2 (FIG. 5).

In this way, the device prevents the crystallization of the chromophores through site-isolation, thereby realizing superior stability, unlike general organic glass materials. In the TBC test, the device may endure 140 V per μm, and realizes considerably superior stability than conventional devices, which are incapable of enduring 100 V or more per μm. Further, the coupling speed, which is conventionally problematic in the TBC test, is greatly improved.

In addition, the exemplary embodiments provide a method of manufacturing the photorefractve device.

The method of manufacturing the device includes i) forming a keyhole-shaped indium fin oxide transparent electrode on a glass substrate, ii) dropping the prepared photorefractve dendrimer on the electrode, drying it to remove the solvent, and conducting vacuum drying, iii) binding a spacer to the corners of the dried indium fin oxide-glass sample, heating the sample to a temperature above a glass transparent temperature, slowly pressing another indium tin oxide glass substrate on the glass sample, and conducting cooling, and iv) enclosing the substrates using epoxy or a polyimide film, and attaching an electrode thereto.

In the method of manufacturing the photorefractve device, the spacer may be an imide film 60 mm thick.

A better understanding of exemplary embodiments may be obtained in light of the following examples, which are set forth to illustrate, but are not to be construed to limit example embodiments.

EXAMPLE 1

Preparation of 9-(6-(tert-butyldimethylsilyloxy) hexyl)-9H-carbazole-3-carbaldehyde (4)

9-(6-hydroxyhexyl)-9H-carbazole-3-carbaldehyde (12.0 g, 0.0406 mol) and dichloromethane (100 ml) were loaded into a three-neck flask, stirred, added with tert-butyldimethylsilyl chloride (7.35 g, 0.0487 mol) and imidazole (3.04 g, 0.0447 mol), and allowed to react at room temperature for 24 hours with stirring. The reaction product was transferred into a separate funnel, and was then added with water and ethyl acetate, after which the organic layer was isolated therefrom, dehydrated using sodium sulfate, and then distilled under reduced pressure. Then, the obtained viscous liquid was separated through silica column chromatography, thus obtaining 10.8 g of a liquid as the title compound.

The NMR data of the above material was as follows:
$^1$H NMR (400 MHz, CDCl$_3$, rt): δ (ppm) 0.01 (s, 6H, CH$_3$Si) 0.87 (s, 9H, CH$_3$), 1.36~1.38 (m, 4H, CH$_2$), 1.44~1.50 (m, 2H, CH$_2$), 1.82~1.90 (m, 2H, CH$_2$), 3.55 (t, J=6.0 Hz, 2H, OCH$_2$), 4.28 (t, J=6.8 Hz, 2H, NCH$_2$), 7.30 (t, J=7.6 Hz, 1H, aromatic protons), 7.43 (d, J=8.4 Hz, 2H, aromatic protons), 7.51 (t, J=7.2 Hz, 1H, aromatic protons), 7.98 (d, J=7.8 Hz, 1H, aromatic protons), 8.13 (d, J=7.5 Hz, 1H, aromatic protons), 8.60 (s, 1H, aromatic protons), 10.1 (s, 1H, CHO)

EXAMPLE 2

Preparation of (9-(6-(tert-butyldimethylsilyloxy) hexyl)-9H-carbazol-3-yl)methanol (5)

In a three-neck flask, 9-(6-hydroxyhexyl)-9H-carbazole-3-carbaldehyde (12.0 g, 0.0406 mol), dichloromethane (100 ml), and sodium borohydride (0.55 g, 0.0147 mol) were dissolved in 100 ml of methanol, after which the reaction solution was allowed to react at 60° C. for 3 hours with stirring. The reaction product was transferred into a separate funnel, and was then added with water and ethyl acetate, after which the organic layer was isolated therefrom, dehydrated using sodium sulfate, and then distilled under reduced pressure. Thereafter, the obtained viscous liquid was separated through silica column chromatography, thus obtaining 9.0 g of a yellowish transparent liquid material.

The NMR data of the above material was as follows.
$^1$H NMR (400 MHz, CDCl$_3$, rt): δ (ppm) 0.06 (s, 9H, CH$_3$) 0.92 (s, 9H, CH$_3$Si), 1.36~1.38 (m, 4H, CH$_2$), 1.46~1.52 (m, 2H, CH$_2$), 1.82~1.89 (m, 2H, CH$_2$), 2.14 (s, 1H, OH), 3.55 (t, J=6.0 Hz, 2H, OCH$_2$), 4.28 (t, J=6.8 Hz, 2H, NCH$_2$), 4.83 (s, 2H, CH$_2$OH), 7.24 (t, J=7.6 Hz, 1H, aromatic protons), 7.37 (d, J=8.0 Hz, 1H, aromatic protons), 7.41 (d, J=8.0 Hz, 1H, aromatic protons), 7.48 (m, 2H, aromatic protons), 8.09 (d, J=6.0 Hz, 2H, aromatic protons).

EXAMPLE 3

Preparation of 6-((2-ethylhexyl)(phenyl)amino)hexyl acetate (6)

6-((2-ethylhexyl)(phenyl)amino)hexan-1-ol (8.0 g, 0.023 mol) and dichloromethane (100 ml) were loaded into a three-neck flask, stirred, and added with acetic anhydride (2.8 g, 0.028 mol) and pyridine (3.0 g, 0.038 mol). The mixture was allowed to react at 40° C. for 12 hours with stirring. The reaction product was transferred into a separate funnel, and was then added with water and dichloromethane, after which the organic layer was isolated therefrom, dehydrated using sodium sulfate, and then distilled under reduced pressure. Subsequently, the obtained viscous liquid was separated through silica column chromatography, thus obtaining 7.5 g of a yellowish transparent liquid.

The NMR data of the above material was as follows.

$^1$H NMR (300 MHz, CDCl$_3$, rt): δ (ppm) 0.89 (t, J=7.5 Hz, 6H, CH$_3$), 1.28 (m, J=4.2 Hz, 12H, CH$_2$), 1.56 (m, J=7.5 Hz, 4H, CH$_2$), 1.69 (m, J=4.2 Hz, 1H, CH), 2.04 (s, 3H, CH$_3$C), 3.14 (d, J=6.9 Hz, 2H, NCH$_2$) 3.28 (t, J=6.0 Hz 2H, NCH$_2$), 4.05 (t, J=6.6 Hz, 2H, OCH$_2$), 6.61 (t, J=7.2 Hz, 1H, aromatic protons), 6.66 (d, J=7.8 Hz, 2H, aromatic protons), 7.19 (t, J=7.5 Hz, 2H, aromatic protons).

EXAMPLE 4

Preparation of 6-((4-(4-cyano-5-(dicyanomethylene)-2-oxo-2,5-dihydro-1H-pyrrol-3-yl)phenyl)(2-ethylhexyl)amino)hexyl acetate (7)

In a three-neck flask, 6-((2-ethylhexyl)(phenyl)amino) hexyl acetate (7.0 g, 0.020 mol) was dissolved in dimethylformamide (100 ml), stirred, and added with acetic anhydride (2.9 g, 0.028 mol) and 4-cyano-5-dicyanomethylene-3-hydroxy-2-oxo-3-pyrroline disodium salt (5.6 g, 0.024 mol). The temperature was decreased to 0° C., after which POCl$_3$ was slowly added thereto for 30 min, and the mixture was allowed to react at room temperature for 6 hours with stirring. A solid product was precipitated with water, filtered, and then dried, thus obtaining 4.0 g of a dark blue solid.

The NMR data of the above material was as follows.

$^1$H NMR (400 MHz, CDCl$_3$, rt): δ (ppm) 0.91 (t, J=7.5 Hz, 6H, CH$_3$), 1.28 (m, J=4.2 Hz, 12H, CH$_2$), 1.56 (m, J=7.5 Hz, 4H, CH$_2$), 1.69 (m, J=4.2 Hz, 1H, CH), 2.04 (s, 3H, CH$_3$C), 3.12 (d, J=7.6 Hz, 2H, NCH$_2$) 3.23 (t, J=6.0 Hz, 2H, NCH$_2$), 4.05 (t, J=6.6 Hz, 2H, OCH$_2$), 6.77 (d, J=6.0 Hz, 2H, aromatic protons), 8.54 (d, J=6.0 Hz, 2H, aromatic protons), 9.09 (s, 1H, NH).

EXAMPLE 5

Preparation of 2(1-(6-(9H-carbazol-9-yl)hexyl)-3-cyano-4-(4-((2-ethylhexyl)(6-hydroxyhexyl)amino) phenyl)-5-oxo-1H-pyrrol-2(5H)-ylidene)malononitrile (8)

In a three-neck flask, 6-((2-ethylhexyl)(phenyl)amino) hexyl acetate (3.0 g, 5.82 mmol) and sodium carbonate (2.3 g, 2.91 mmol) were dissolved in dimethylformamide (50 ml) and stirred. The mixture was heated to 90° C., added with 9-(6-bromohexyl)-9H-carbazole (2.30 g, 7.00 mmol) and then stirred for 24 hours. A blue solid was precipitated with ice water, dehydrated using sodium sulfate, and then distilled under reduced pressure. Then, the obtained viscous liquid was separated through silica column chromatography, yielding 4.00 g of a dark blue solid (6-((4-(6-(9H-carbazol-9-yl) hexyl-4-cyano-5-(dicyanomethyl)-2-oxo-2,5-dihydro-1H-pyrrol-3-yl)phenyl(2-ethylhexyl)amino)hexyl acetate).

In a three-neck flask, the prepared 6-((4-(6-(9H-carbazol-9-yl)hexyl)-4-cyano-5-(dicyanomethyl)-2-oxo-2,5-dihydro-1H-pyrrol-3-yl)phenyl(2-ethylhexyl)amino)hexyl acetate (3.5 g, 4.50 mmol) was added to tetrahydrofuran (50 ml) and stirred. The mixture was added with hydrochloric acid (10 ml, 3 N) and stirred at 65° C. for 24 hours. The obtained solution was transferred into a separate funnel, and was then added with water and dichloromethane, after which the organic layer was isolated therefrom, dehydrated using sodium sulfate, and then distilled under reduced pressure. Subsequently, the obtained material was separated through silica column chromatography, thus obtaining 3.0 g of a dark blue solid.

The NMR data of the above material was as follows.

$^1$H NMR (300 MHz, CDCl$_3$, rt): δ (ppm) 0.94 (t, J=8.0 Hz, 6H, CH$_3$), 1.32~1.44 (m, 16H, CH$_2$), 1.54~1.66 (m, 6H, CH$_2$), 1.68 (t, J=8.0 Hz, 1H, HOC) 1.78~1.90 (m, 3H, CH$_2$), 3.35 (d, J=7.6 Hz, 2H, NCH$_2$) 3.44 (t, J=7.0 Hz, 2H, NCH$_2$), 3.96 (t, J=6.6 Hz, 2H, NCH$_2$), 4.05 (t, J=6.7 Hz, 2H, OCH$_2$), 4.29 (t, J=7.0 Hz, 2H, NCH$_2$), 6.73 (t, J=8.7 Hz, 2H, aromatic protons), 7.19 (t, J=8.7 Hz, 2H, aromatic protons), 7.19 (t, J=8.7 Hz, 2H, aromatic protons), 7.39 (d, J=8.7 Hz, 2H, aromatic protons), 7.46 (t, J=8.7 Hz, 2H, aromatic protons), 8.07 (d, J=8.7 Hz, 2H, aromatic protons), 8.46 (d, J=8.7 Hz, 2H, aromatic protons).

EXAMPLE 6

Preparation of methyl 6-((2-ethylhexyl)(phenyl)amino)hexanoate (9)

In a three-neck flask, methyl 6-(phenylamino)hexanoate (25.0 g, 0.113 mmol) and potassium carbonate (25.0 g, 0.169 mol) were added to dimethylformamide (100 ml) and stirred. The mixture was heated to 100° C., added with 3-(bromomethyl)heptane (26.2 g, 0.135 mol), and allowed to react with stirring for 12 hours. The reaction product was transferred into a separate funnel, and was then added with water and ethyl acetate, after which the organic layer was isolated therefrom, dehydrated using sodium sulfate, and then distilled under reduced pressure. Subsequently, the obtained material was separated through silica column chromatography, thus obtaining 20.0 g of a yellowish transparent liquid.

The NMR data of the above material was as follows.

$^1$H NMR (300 MHz, CDCl$_3$, rt): δ (ppm) 0.91 (t, J=7.5 Hz, 6H, CH$_3$), 1.28~1.42 (m, J=4.2 Hz, 10H, CH$_2$), 1.56 (m, J=7.5 Hz, 4H, CH$_2$), 1.69 (m, J=4.2 Hz, 1H, CH), 2.04 (s, 3H, CH$_3$C), 3.14 (d, J=7.6 Hz, 2H, NCH$_2$) 3.28 (t, J=6.0 Hz, 2H, NCH$_2$), 4.05 (t, J=6.6 Hz, 2H, OCH$_2$), 6.61 (t, J=7.2 Hz, 1H, aromatic protons), 6.66 (d, J=7.8 Hz, 2H, aromatic protons), 7.19 (t, J=7.5 Hz, 2H, aromatic protons).

EXAMPLE 7

Preparation of methyl 6-((4(4-cyano-5-(dicyanomethylene)-2-oxo-2,5-dihydro-1H-pyrrol-3-yl)phenyl) (2-ethylhexyl)amino)hexanoate (10)

In a three-neck flask 6-((2-ethylhexyl)(phenyl)amino) hexyl acetate (7.0 g, 0.020 mol) was added to dimethylformamide (100 ml), stirred, and then added with acetic anhydride (2.9 g, 0.028 mol) and 4-cyano-5-dicyanomethylene-3- hydroxy-2-oxo-3-pyrroline disodium salt (5.6 g, 0.024 mol). The temperature was decreased to 0° C., POCl₃ was slowly added thereto for 30 min, and then the mixture was allowed to react at room temperature for 6 hours with stirring. A solid product was precipitated with water, filtered, and then dried, thus obtaining 4.0 g of a dark blue solid.

The NMR data of the above material was as follows.

$^1$H NMR (400 MHz, CDCl₃, rt): δ (ppm) 0.91 (t, J=7.5 Hz, 6H, CH₃), 1.28~1.32 (m, J=4.2 Hz, 12H, CH₂), 1.56 (m, J=7.5 Hz, 4H, CH₂), 1.69 (m, J=4.2 Hz, 1H, CH), 2.04 (s, 3H, CH₃C), 3.12 (d, J=7.6 Hz, 2H, NCH₂), 3.23 (t, J=6.0 Hz, 2H, NCH₂), 4.05 (t J=6.6 Hz, 2H, OCH₂), 6.77 (d, J=6.0 Hz, 2H, aromatic protons), 8.54 (d, J=6.0 Hz, 2H, aromatic protons), 9.09 (s, 1H, NH).

EXAMPLE 8

Preparation of 6-((4-(4-cyano-5-(dicyanomethylene)-1-hexyl-2-oxo-2,5-dihydro-1H-pyrrol-3-yl)phenyl)(2-ethylhexyl)amino)hexanoic acid (11)

In a three-neck flask, methyl 6-((4-(4-cyano-5-(dicyanomethylene)-2-oxo-2,5-dihydro-1H-pyrrol-3-yl)phenyl)(2-ethylhexyl)amino)hexanoate (8.0 g, 15.9 mmol) and potassium carbonate (1.1 g, 7.97 mmol) were added to dimethylformamide (50 ml) and stirred. The mixture was heated to 90° C., added with 1-bromohexane (3.16 g, 19.1 mmol), and allowed to react with stirring for 24 hours. After the reaction, the resultant product was precipitated using ice water, thus obtaining a blue solid, which was then subjected to dehydration using sodium sulfate and to distillation under reduced pressure. Subsequently, the obtained material was separated through silica column chromatography, yielding 8.00 g of a dark blue solid (methyl 6-((4-(4-cyano-5-(dicyanomethylene)-1-hexyl-2-oxo-2,5-dihydro-1H-pyrrol-3-yl)phenyl)(2-ethylhexyl)amino)hexanoate).

The prepared methyl 6-((4-(4-cyano-5-(dicyanomethylene)-1-hexyl-2-oxo-2,5-dihydro-1H-pyrrol-3-yl)phenyl)(2-ethylhexyl)amino)hexanoate (7.5 g, 12.8 mmol) and tetrahydrofuran (50 ml) were loaded into a flask and stirred. Hydrochloric acid (20 ml, 3 N) was added thereto, and the mixture was allowed to react at 65° C. for 24 hours with stirring. The reaction product was transferred into a separate funnel, and was then added with water and dichloromethane, after which the organic layer was isolated therefrom, dehydrated using sodium sulfate, and then distilled under reduced pressure. Subsequently, the obtained material was separated through silica column chromatography, thus obtaining 6.4 g of a dark blue solid.

The NMR data of the material was as follows.

$^1$H NMR (300 MHz, CDCl₃, rt): δ (ppm) 0.87 (t, J=8.0 Hz, 9H, CH₃), 1.28~1.43 (m, 16H, CH₂), 1.60~1.71 (m, 6H, CH₂), 1.82 (t, J=4.0 Hz, 1H, HC), 2.37 (t, 2H, J=7.6 Hz, CH₂CO), 3.35 (d, J=7.6 Hz, 2H, NCH₂), 3.46 (t, J=7.0 Hz, 2H, NCH₂), 4.02 (t, J=6.7 Hz, 2H, NCH₂), 6.73 (t, J=8.7 Hz, 2H, aromatic protons), 8.46 (d, J=8.7 Hz, 2H, aromatic protons).

EXAMPLE 9

Preparation of (946-(tert-butyldimethylsilyloxy) hexyl)-9H-carbazol-3-yl)methyl 6-((4-(4-cyano-5-(dicyanomethylene)-1-hexyl-2-oxo-2,5-dihydro-1H-pyrrol-3-yl)phenyl)(2-ethylhexyl)amino) hexanoate (12)

In a three-neck flask, 6-((2-ethylhexyl)(phenyl)amino) hexyl acetate (2.74 g, 6.65 mmol) and 6-((4-(4-cyano-5-(dicyanomethylene)-1-hexyl-2-oxo-2,5-dihydro-1H-pyrrol-3-yl)phenyl)(2-ethylhexyl)amino)hexanoic acid (3.80 g, 6.65 mmol), DPTS (1.5 g, 5.32 mmol), and dicyclohexylcarbodiimide (1.56 g, 5.32 mmol) were dissolved in dichloromethyl (50 ml) and the solution was allowed to react at room temperature for 24 hours with stirring. The precipitate was filtered, and was then distilled under reduced pressure. Then, the obtained viscous liquid was separated through silica column chromatography, thus obtaining 3.1 g of a dark blue solid as the title compound.

The NMR data of the above material was as follows.

$^1$H NMR (300 MHz, CDCl₃, rt): δ (ppm) 0.01 (s, 6H, CH₃Si), 0.70~1.02 (m, 18H, CH₃), 1.20~1.49 (m, 22H, CH₂), 1.60~1.86 (m, 9H, CH₂), 2.38 (t, 2H, J=7.6 Hz, CH₂CO), 3.31 (d, J=7.6 Hz, 2H, NCH₂), 3.41 (t, J=7.0 Hz, 2H, NCH₂), 3.55 (t, J=7.2 Hz, 2H, NCH₂), 3.99 (t, J=7.0 Hz, 2H, NCH₂), 4.28 (t, J=7.3 Hz, 2H, OCH₂), 5.28 (s, 2H, OCH₂Ar), 6.70 (d, J=8.7 Hz, 2H, aromatic protons), 7.21 (t, J=8.7 Hz, 2H, aromatic protons), 7.37 (d, J=8.7 Hz, 2H, aromatic protons), 7.45 (t, J=8.7 Hz, 2H, aromatic protons), 8.07 (d, J=8.7 Hz, 2H, aromatic protons), 8.45 (d, J=8.7 Hz, 2H, aromatic protons).

EXAMPLE 10

Preparation of (946-hydroxyhexyl)-9H-carbazol-3-yl)methyl 6-((4-(4-cyano-5-(dicyanomethylene)-1-hexyl-2-oxo-2,5-dihydro-1H-pyrrol-3-yl)phenyl)(2-ethylhexyl)amino)hexanoate (13)

In a flask, (9-(6-(tert-butyldimethylsilyloxy)hexyl)-9H-carbazol-3-yl)methyl 6-((4-(4-cyano-5-(dicyanomethylene)-1-hexyl-2-oxo-2,5-dihydro-1H-pyrrol-3-yl)phenyl)(2-ethylhexyl)amino)hexanoate (2.5 g, 2.6 mmol) was added to tetrahydrofuran (50 ml) and stirred. The stirred solution was added with hydrochloric acid (10 ml, 3 N) and allowed to react at 65° C. for 24 hours with stirring. The reaction product was transferred into a separate funnel, added with water and dichloromethane, after which the organic layer was isolated therefrom, dehydrated using sodium sulfate, and then distilled under reduced pressure. Then, the obtained material was separated through silica column chromatography, thus obtaining 1.6 g of a dark blue solid.

The NMR data of the material was as follows.

$^1$H NMR (300 MHz, CDCl₃, rt): δ (ppm) 0.89~0.94 (m, 9H, CH₃), 1.30~1.49 (m, 22H, CH₂), 1.60~1.86 (m, 9H, CH₂), 2.38 (t, 2H, J=7.6 Hz, CH₂CO), 3.34 (d, J=7.6 Hz, 2H, NCH₂), 3.41 (t, J=7.0 Hz, 2H, NCH₂), 3.55 (t, J=7.2 Hz, 2H, NCH₂), 3.99 (t, J=7.0 Hz, 2H, NCH₂), 4.28 (t, J=7.3 Hz, 2H, OCH₂), 5.28 (s, 2H, OCH₂Ar), 6.70 (d, J=8.7 Hz, 2H, aromatic protons), 7.21 (t, J=8.7 Hz, 2H, aromatic protons), 7.37 (d, J=8.7 Hz, 2H, aromatic protons), 7.45 (t, J=8.7 Hz, 2H, aromatic protons), 8.07 (d, J=8.7 Hz, 2H, aromatic protons), 8.45 (d, J=8.7 Hz, 2H, aromatic protons).

EXAMPLE 11

Preparation of Photorefractve Dendrimer 1 (14)

In a three-neck flask, 2-(1-(6-(9H-carbazol-9-yl)hexyl)-3-cyano-4-(4-((2-ethylhexyl)(6-hydroxyhexyl)amino)phenyl)-5-oxo-1H-pyrrol-2(5H)-ylidene)malononitrile (1.5 g, 2.07 mmol) and 6,6',6"-(4,4',4"-(ethane-1,1,1-trinyl)tris(4,1-phenylene))tris(oxy)trihexanoic acid (0.41 g, 0.622 mmol) were dissolved in chloromethyl (50 ml) and stirred. The mixture was added with DPTS (0.49 g, 1.66 mmol) and dicyclohexylcarbodiimide (0.85 g, 4.14 mmol) and stirred at room temperature for 24 hours. The precipitate was filtered and distilled under reduced pressure. Thereafter, the obtained solid was separated through silica column chromatography, thus obtaining 1.25 g of a dark blue solid.

The NMR data of the material was as follows.

$^1$H NMR (300 MHz, CDCl$_3$, rt): δ (ppm) 0.90 (t, 18H, CH$_3$), 1.28~1.46 (m, 56H, CH$_2$), 1.59~1.69 (m, 26H, CH$_2$), 1.72~1.79 (m, 10H, CH$_2$), 1.83~1.90 (m, 7H, CH$_2$), 2.06 (s, 3H, CH$_3$CPh$_3$), 2.31 (t, 6H, J=7.6 Hz CH$_2$CO), 3.34 (d, J=7.6 Hz, 6H, NCH$_2$), 3.43 (t, J=7.0 Hz, 6H, NCH$_2$), 3.88 (t, J=7.2 Hz, 6H, NCH$_2$), 3.95 (t, J=7.0 Hz, 6H, NCH$_2$), 4.05 (t, J=7.3 Hz, 6H, OCH$_2$), 4.28 (t, J=7.2 Hz, 6H, NCH$_2$), 6.72 (q, 12H, aromatic protons), 6.95 (d, J=8.7 Hz, 6H, aromatic protons), 7.19 (t, J=8.7 Hz, 6H, aromatic protons), 7.36 (d, J=8.7 Hz, 6H, aromatic protons), 7.43 (t, J=8.7 Hz, 6H, aromatic protons), 8.06 (d, J=8.7 Hz, 6H, aromatic protons), 8.45 (d, J=8.7 Hz, 6H, aromatic protons).

EXAMPLE 12

Preparation of Photorefractive Dendrimer 2 (15)

In a three-neck flask, (946-hydrohexyl)-9H-carbazol-3-yl) methyl 6-((4-(4-cyano-5-(dicyanomethylene)-1-hexyl-2-oxo-2,5-dihydro-1H-pyrrol-3-yl)phenyl)(2-ethylhexy) amino)hexanoate (1.5 g, 1.76 mmol) and 6,6',6"-(4,4',4"-(ethane-1,1,1-trinyl)tris(4,1-phenylene))tris(oxy)trihexanoic acid (0.35 g, 0.53 mmol) were dissolved in chloromethyl (50 ml) and stirred. The mixture was added with DPTS (0.414 g, 1.41 mmol) and dicyclohexylcarbodiimide (1.03 g, 3.5 mmol) and stirred at room temperature for 24 hours. The precipitate was filtered and distilled under reduced pressure. Thereafter, the obtained solid was separated through silica column chromatography, thus obtaining 1.26 g of a dark blue solid.

The NMR data of the material was as follows.

$^1$H NMR (300 MHz, CDCl$_3$, rt): δ (ppm) 0.88 (t, 27H, CH$_3$) 1.22~1.40 (m, 54H, CH$_2$), 1.45~1.61 (m, 18H, CH$_2$), 1.62~1.79 (m, 32H, CH$_2$), 1.78~1.88 (m, 7H, CH$_2$), 2.05 (s, 3H, CH$_3$CPh$_3$), 2.27 (t, 6H, J=7.6 Hz, CH$_2$CO), 2.37 (t, 6H, J=7.6 Hz, CH$_2$CO), 3.31 (d, J=7.6 Hz, 6H, NCH$_2$), 3.40 (t, J=7.0 Hz, 6H, NCH$_2$), 3.88 (t, J=7.2 Hz, 6H, NCH$_2$), 4.00 (t, J=7.0 Hz, 6H, NCH$_2$), 4.27 (t, J=7.3 Hz, 6H, OCH$_2$), 5.27 (s, CH$_2$OH), 6.71 (q, 12H, aromatic protons), 6.95 (d, J=8.7 Hz, 6H, aromatic protons), 7.23 (t, J=8.7 Hz, 3H, aromatic protons), 7.36 (t, J=8.7 Hz, 6H, aromatic protons), 7.44 (t, J=8.7 Hz, 6H, aromatic protons), 8.06 (d, J=8.7 Hz, 6H, aromatic protons), 8.44 (d, J=8.7 Hz, 6H,).

EXAMPLE 13

Manufacture of Photorefractive Device

To compare the properties of the devices of the photorefractive dendrimers (14) and (15) prepared in Examples 11 and 12, the device illustrated in FIG. 1 was manufactured. FIG. 1 schematically illustrates the process of manufacturing the device for evaluating the optical properties of the optical dendrimer compound of the example embodiments. More specifically, to analyze the properties of the device, a glass substrate on which an indium tin oxide transparent electrode was patterned in a keyhole shape was cleaned by washing, after which 3~4 drops of the photorefractive dendrimer, dissolved to 40 wt % in dimethylchloromethane, were dropped thereon at 30° C. The temperature was increased to 80° C. to remove the solvent so that the substrate was sufficiently dried, after which vacuum drying was conducted at 100° C. for 24 hours. A spacer 60 μm thick was bound to the corners of the dried indium tin oxide glass sample. The sample was heated above the glass transition temperature, after which another indium tin oxide glass substrate was slowly pressed on the sample. The glass substrates were cooled to room temperature, and were then sufficiently enclosed using epoxy, after which an electrode was attached thereto, thereby manufacturing a photorefractive device.

EXAMPLE 14

Analysis of Properties of Photorefractive Device

The gain coefficient and birefringence of the photorefractive device thus manufactured were measured.

Specifically, FIG. 2 is a graph illustrating the voltage-gain coefficient of the device representing the glass transition temperature of the optical dendrimer compound of the example embodiments. More specifically, from FIG. 2, showing the glass transition temperature of each of D1 and D2 as DSC data, D1 and D2 could be seen to have glass transition temperatures of 30° C. and 45° C., respectively, which are close to room temperature. In order to allow the non-linear chromophores, which are the structural components of the dendrimer compound, to be easily oriented in the direction of an electric field, the medium should be soft at room temperature. The results of the above graph represent the photorefractive device suitable for use as a medium.

FIG. 3 is a graph illustrating the time-birefringence relationship as a UV spectrum measured for UV-Vis of D1 and D2 in a film form, according to the example embodiments. The reason why D1 and D2 had almost the same spectrum is that they have the same non-linear chromophore and carbazole, and thus the maximum absorption wavelength is formed at 625 nm by the non-linear chromophore and the maximum absorption wavelength is formed at 350 nm by the carbazole.

FIG. 4 is a graph illustrating the birefringence of D1 and D2 using the devices of the optical dendrimer compounds according to example embodiments. Specifically, a TBC test was conducted such that the device was placed between a +45° polarizing plate and a −45° polarizing plate, an electric field was applied thereto, and then light transmittance was determined depending on the time. As illustrated in this drawing, D2, in which the non-linear chromophores were located at the outer parts thereof, could be seen to be easily oriented, resulting in higher birefringence.

FIG. 5 is a graph illustrating the gain coefficient depending on the applied voltage using the devices of the optical dendrimer compounds according to example embodiments. A TBC test is very important in a photorefractve material. Specifically, when two types of light are incident on the photorefractve device, they are transmitted and changed into one bright light and one weak light due to energy transfer, and thus, the gain coefficient may be determined using the degree of brightness, due to the energy transfer, and various experimental conditions. D1 and D2 had similar photoconductivity because the same amount of carbazole was contained therein. However, in FIG. 5, D2 could be seen to have better orientation through the TBC test Further, through the TBC test, D2 could be confirmed to realize much more energy transfer, corresponding to the above result.

In this way, the TBC test resulted in that the device of the example embodiments endured 140 V per μm and had superior stability compared to conventional devices, which are incapable of enduring 100 V or more per μm. The coupling speed, which is conventionally problematic in the TBC test, was seen to be greatly improved.

As described hereinbefore, example embodiments provide a photorefractve dendrimer compound, a method of preparing the same, a photorefractive device using the same, and a method of manufacturing the device. According to example embodiments, the photorefractive dendrimer compound is designed to simultaneously exhibit photoconductivity and electro-optical properties within one compound structure. Dendron has both non-linear optical chromophore and carbazole introduced thereto to thus impart one molecule with photoconductivity and non-linear optical properties at the same time, thereby solving the problems related to the stability of conventional photorefractive materials. Further, the photorefractve dendrimer compound of the example embodiments may be biologically applied, thanks to the use of the non-linear optical chromophore, which is sensitive to near infrared light.

Although preferred example embodiments have been disclosed for illustrative purposes, those skilled in the art will appreciate that various modifications, additions and substitutions are possible, without departing from the scope and spirit of the accompanying claims.

What is claimed is:

1. A photorefractive dendron compound represented by Formulas 1 or 5 below, comprising a non-linear chromophore containing a tricyanopyrroline-based electron-withdrawing group and a carbazole derivative having excellent charge transport properties:

Formula 1

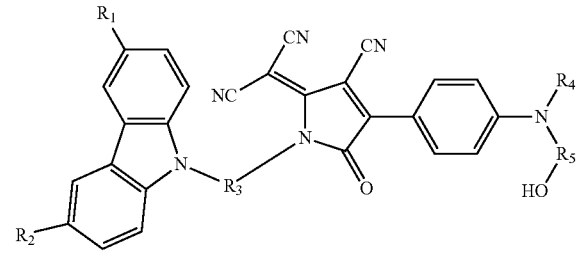

wherein $R_1$, $R_2$ and $R_4$ are each $C_{1-20}$ branched or unbranched alkyl group, and
$R_3$ and $R_5$ are each $C_{1-20}$ alkylene group:

Formula 5

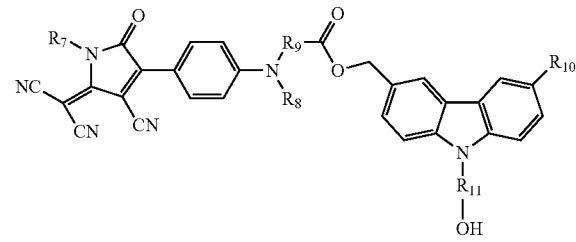

wherein $R_7$, $R_8$ and $R_{10}$ are each $C_{1-20}$ branched or unbranched alkyl group, and
$R_9$ and $R_{11}$ are each $C_{1-20}$ alkylene group.

2. The photorefractive dendron compound as set forth in claim 1, wherein the dendron compound is represented by Formulas 2 or 6 below:

Formula 2

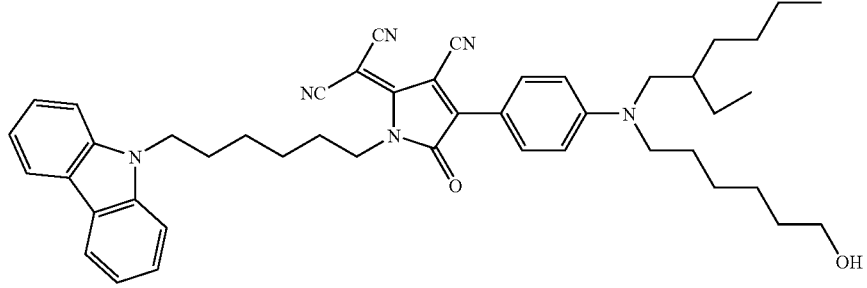

Formula 6

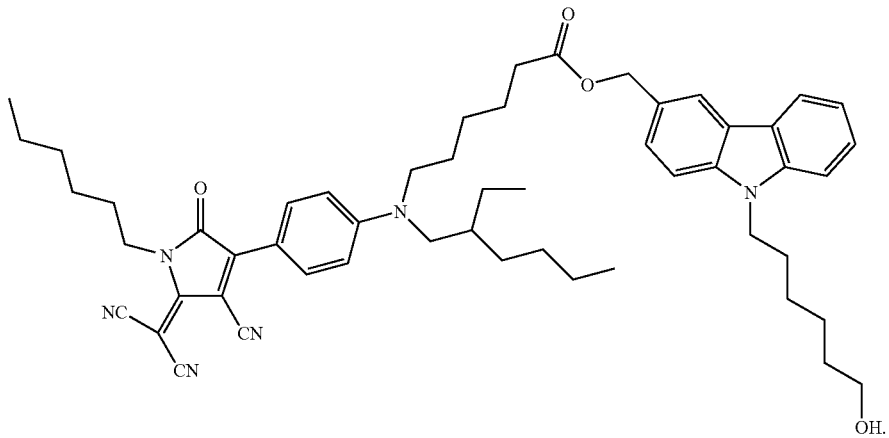

3. A photorefractive dendrimer compound represented by Formulas 3 or 7 below, comprising a non-linear chromophore containing a tricyanopyrroline-based electron-withdrawing group and a carbazole derivative having excellent charge transport properties:

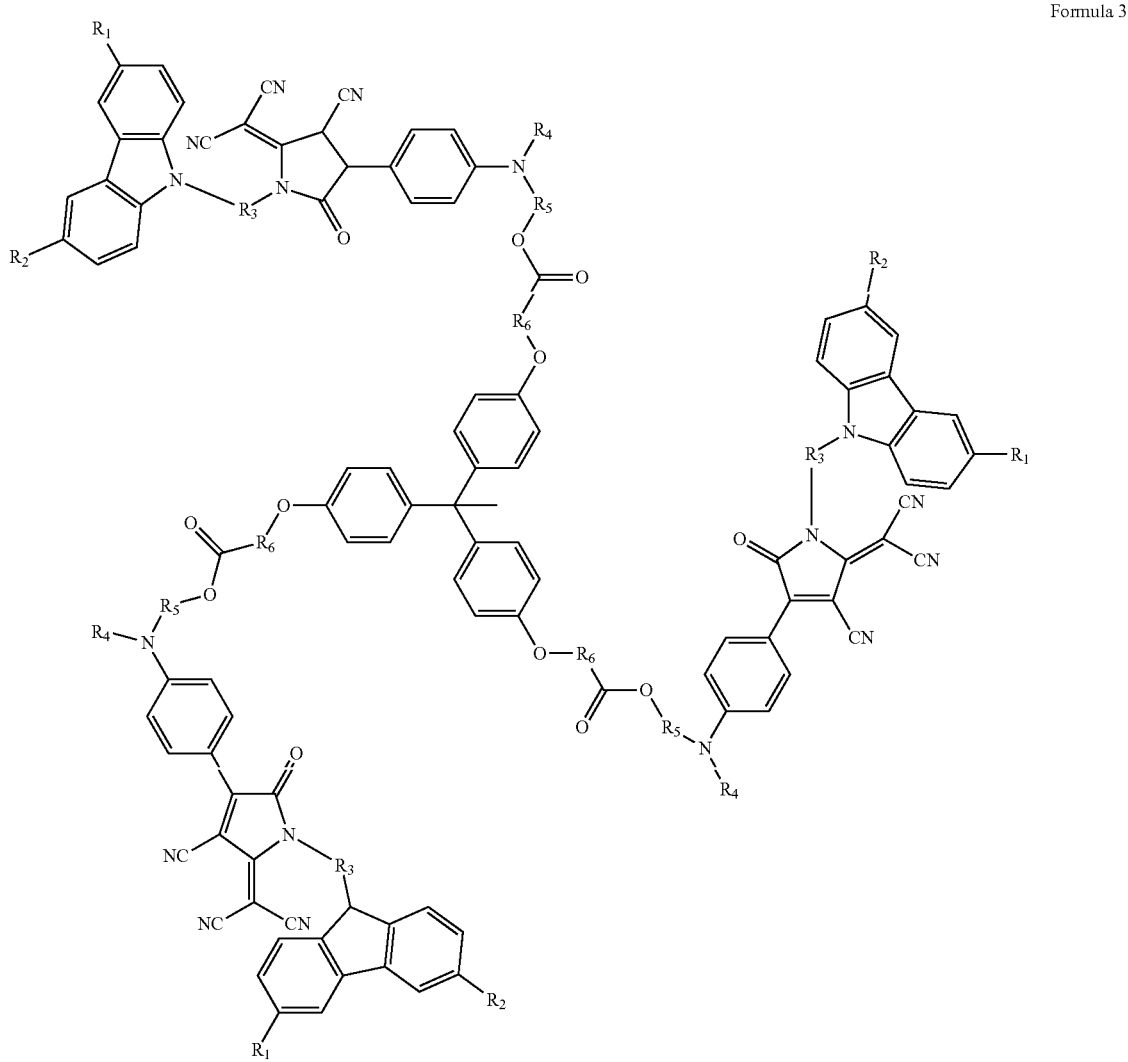

Formula 3 wherein $R_1$, $R_2$ and $R_4$ are each $C_{1-20}$ branched or unbranched alkyl group, and
$R_3$, $R_5$ and $R_6$ are each $C_{1-20}$ alkylene group:

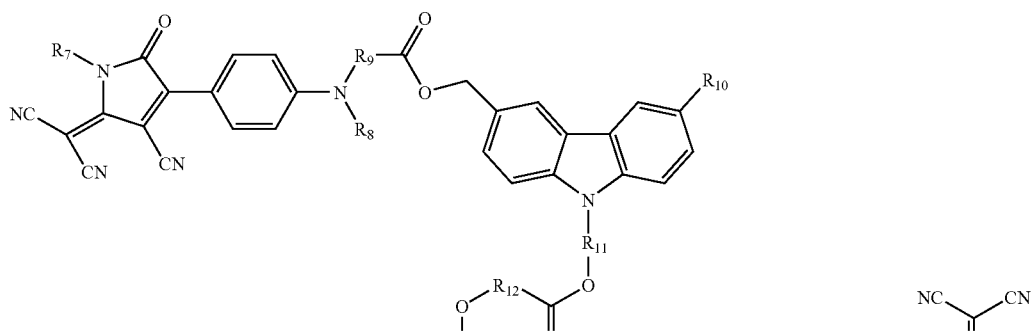

Formula 7

-continued
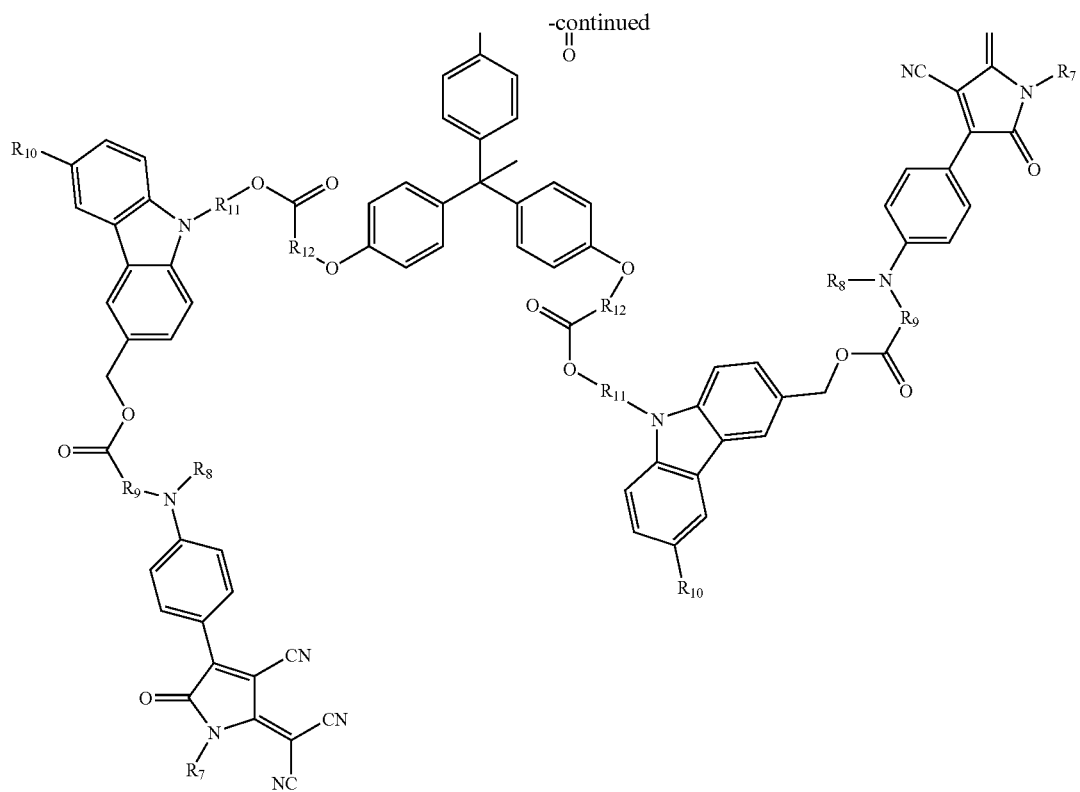
wherein $R_7$, $R_8$ and $R_{10}$ are each $C_{1-20}$ branched or unbranched alkyl group, and
$R_9$, $R_{11}$ and $R_{12}$ are each $C_{1-20}$ alkylene group.
4. The photorefractive dendrimer compound as set forth in claim 3, wherein the dendrimer compound is represented by Formulas 4 or 8 below.
Formula 4
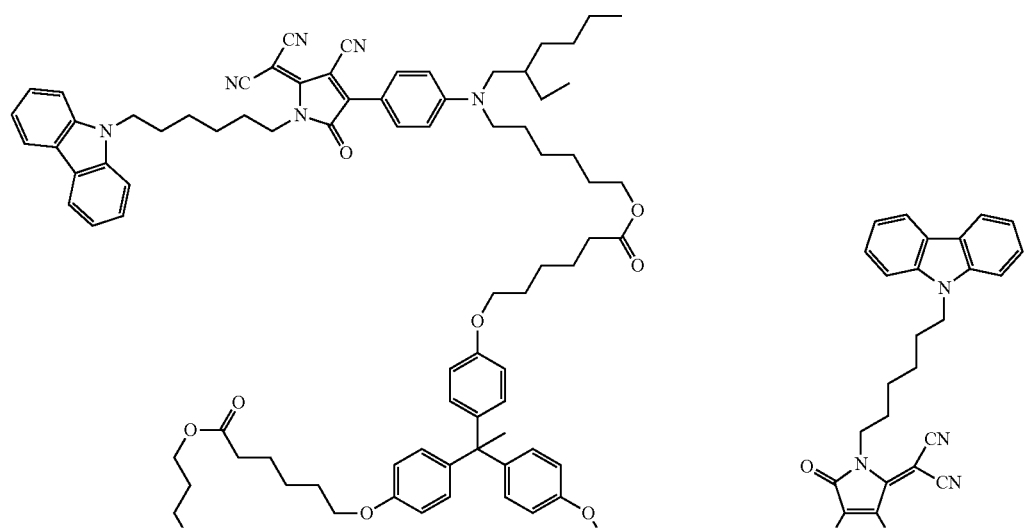

41
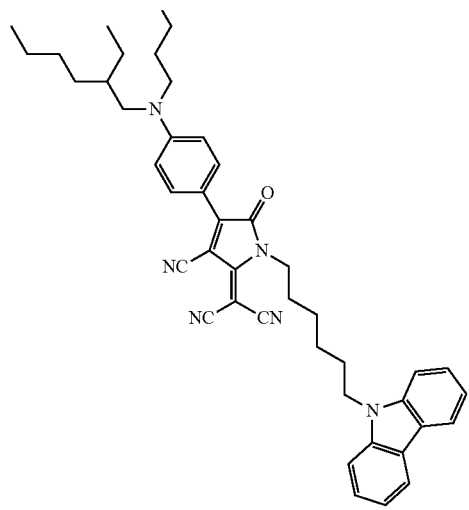
42
-continued
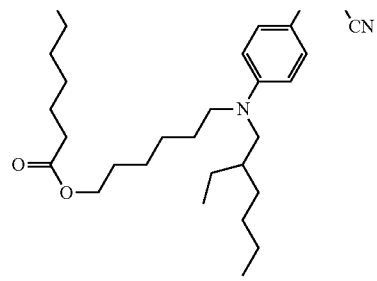
Formula 8
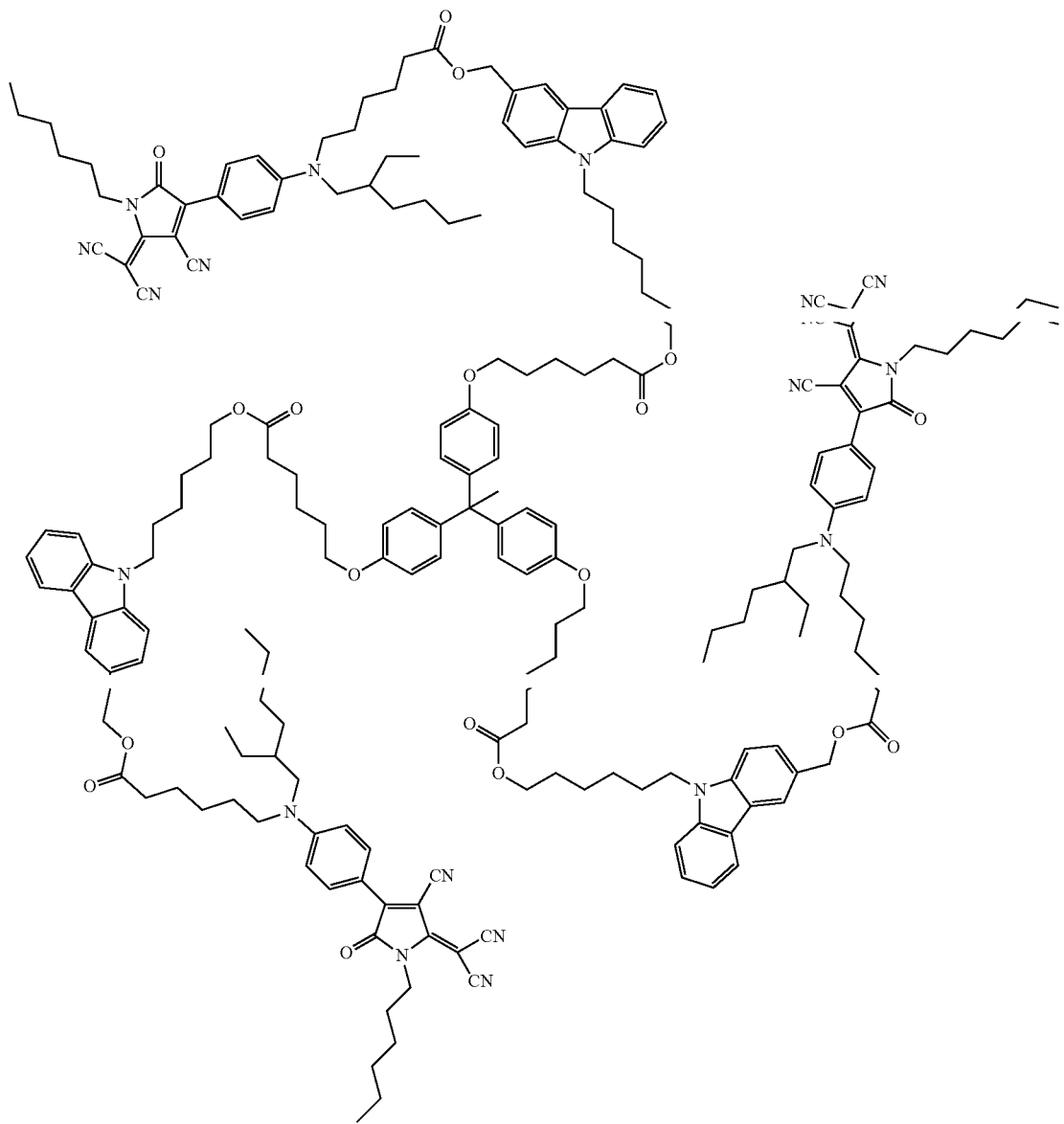

5. A method of preparing the photorefractive dendron compound of claim 2, wherein 2-(1-(6-(9H-carbazol-9-yl)hexyl)-3-cyano-4-(4-((2-ethylhexyl)(6-hydroxyhexyl)amino)phenyl)-5-oxo-1H-pyrrol-2(5H)-ylidene) malononitrile, represented by Formula 2, is prepared through Reaction 4 below.

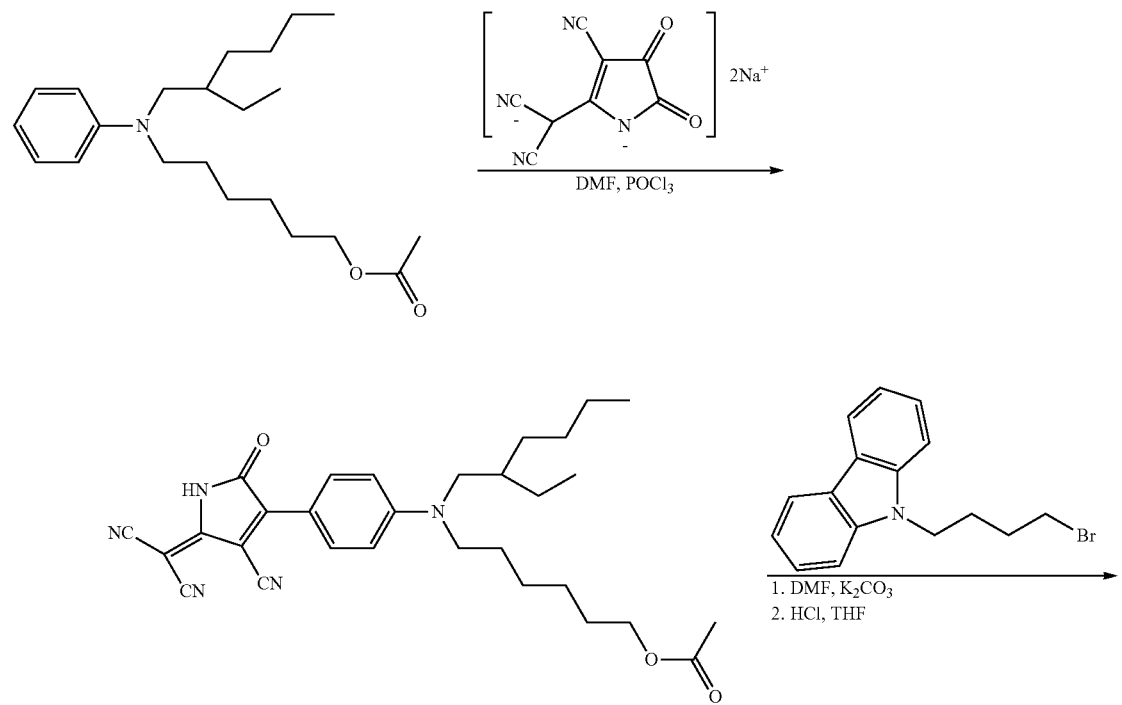

6. A method of preparing the photorefractive dendron compound of claim 2, wherein (9-(6-hydrohexyl)-9H-carbazol-3-yl)methyl6((4-(4-cyano-5-(dicyanomethylene)-1-hexyl-2-oxo-2,5-dihydro-1H-pyrrol-3-yl)phenyl)(2-ethylhexyl)amino)hexanoate, represented by Formula 6, is prepared through Reaction 5 below.

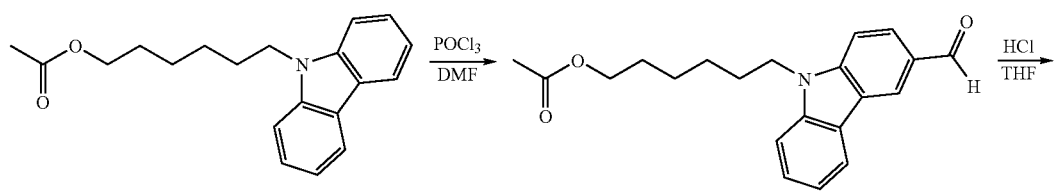

45 46
-continued
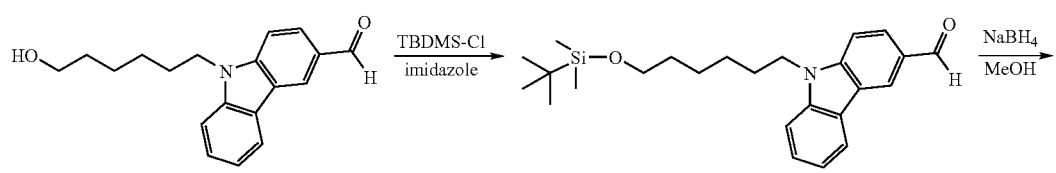
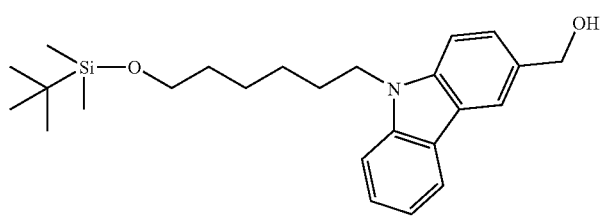
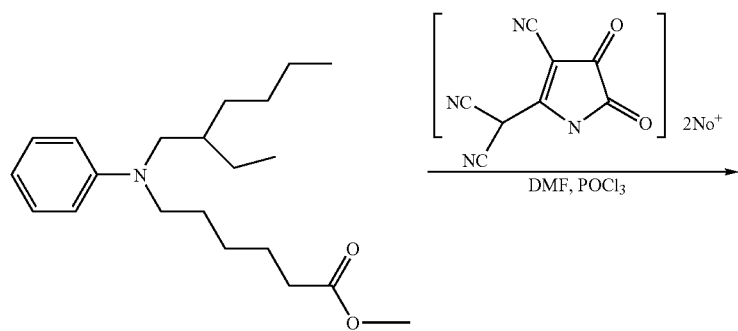
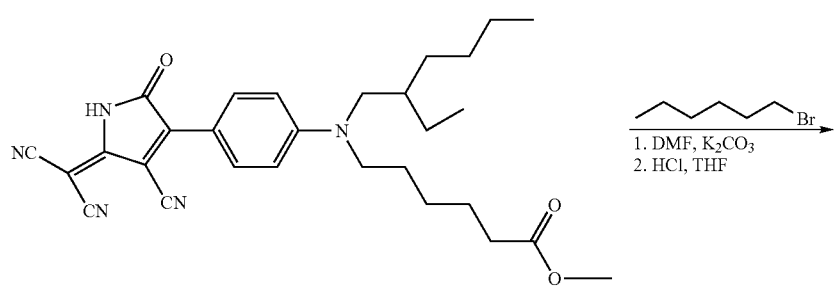
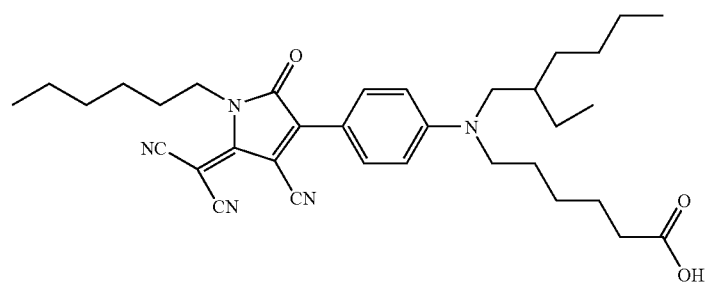

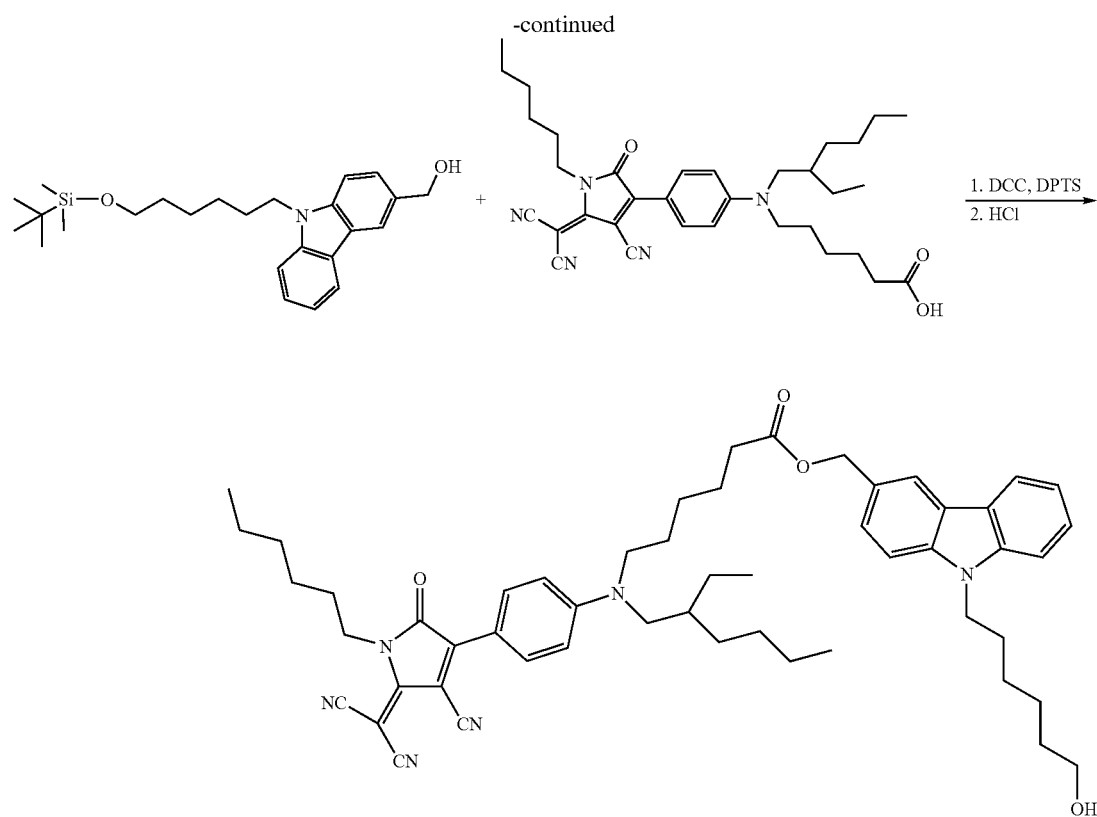
7. A method of preparing the photorefractive dendrimer compound of claim 4, wherein the photorefractive dendrimer compound represented by Formula 4 is prepared through Reaction 4 of claim 5 and Reaction 6 below.
Reaction 6
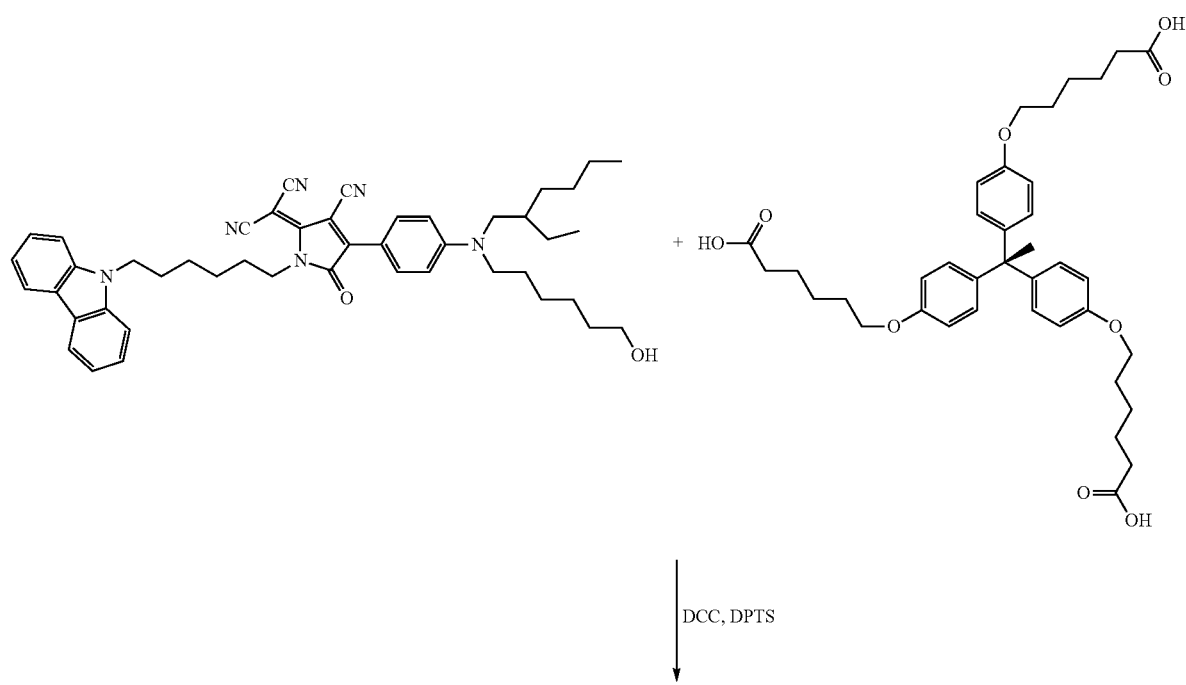

-continued
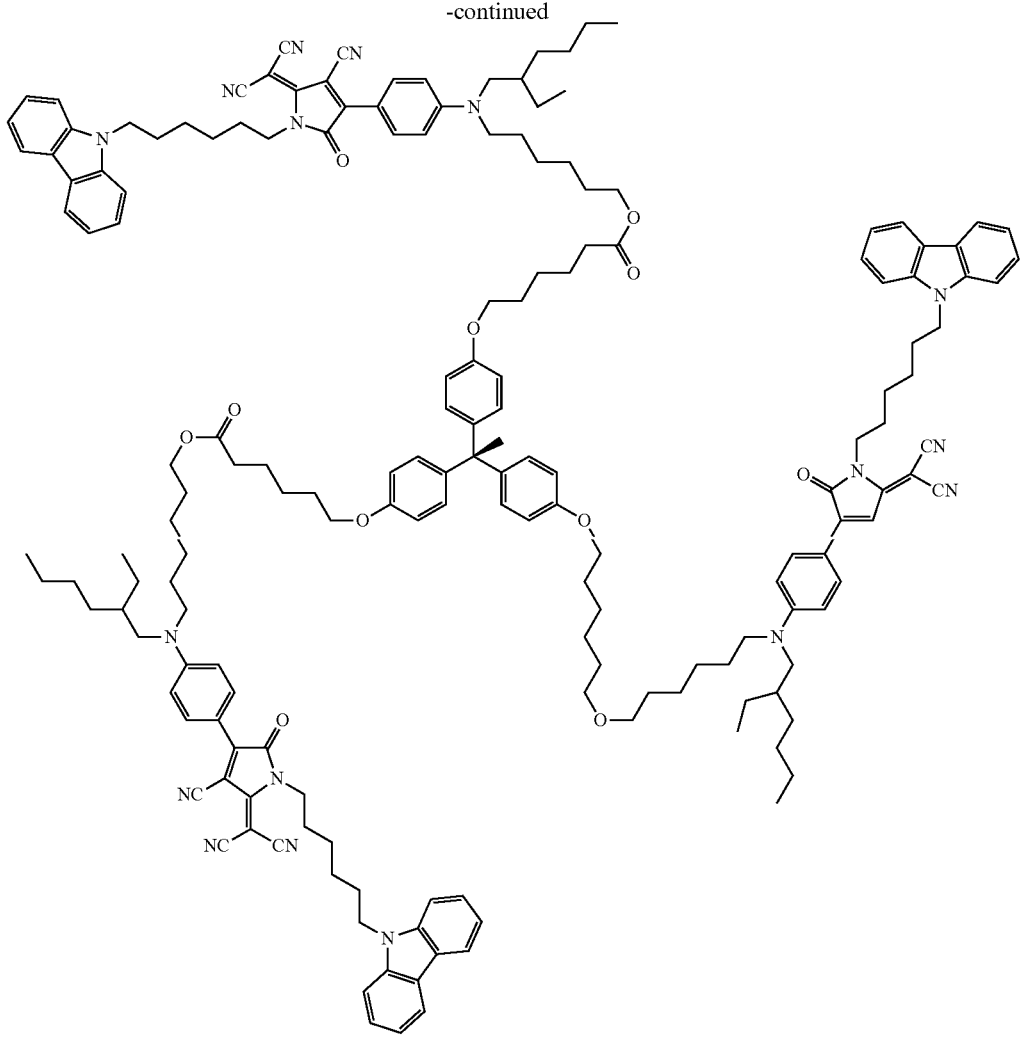
8. A method of preparing the photorefractive dendrimer compound of claim 4, wherein the photorefractive dendrimer compound represented by Formula 8 is prepared through Reaction 5 of claim 6 and Reaction 7 below.
Reaction 7
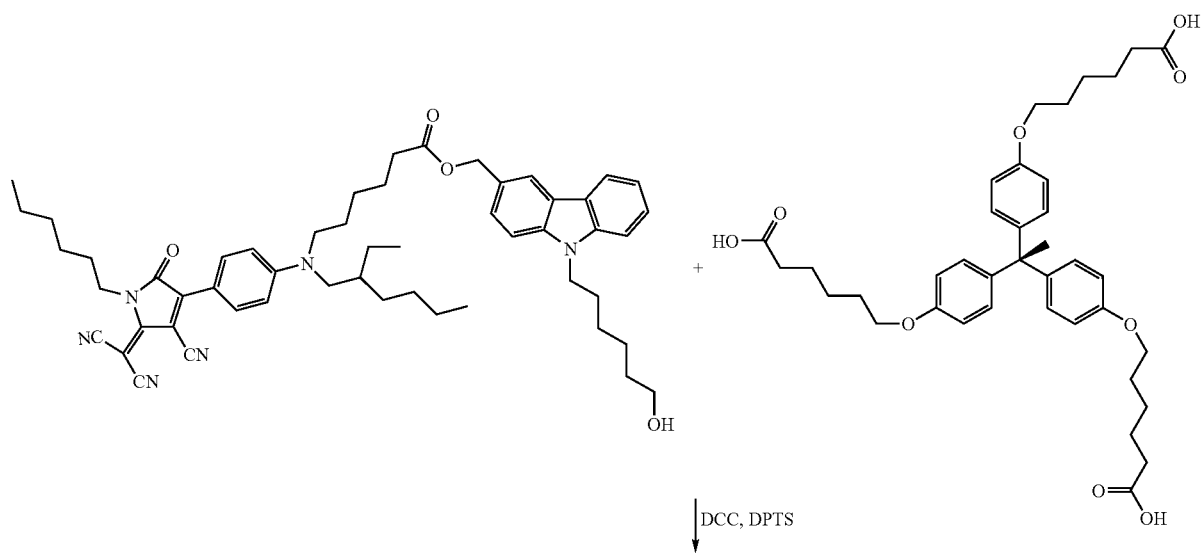

-continued

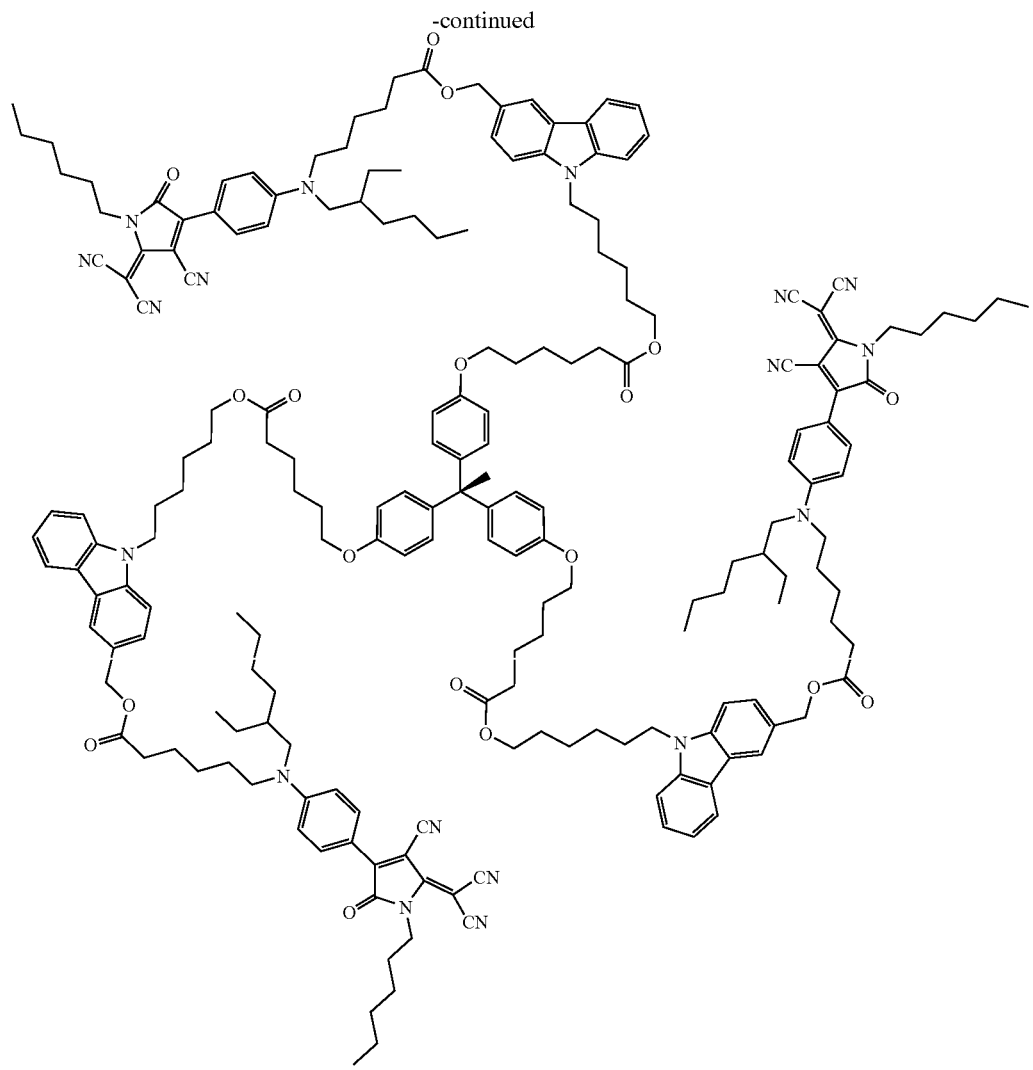

9. A photorefractive device, comprising the photorefractive dendrimer compound of claim 3.

10. A method of manufacturing the photorefractive device of claim 9, comprising:
   i) forming a keyhole-shaped indium tin oxide transparent electrode on a glass substrate;
   ii) dropping the photorefractive dendrimer of claim 4 on the electrode, conducting drying to remove the solvent, and then conducting vacuum drying;
   iii) binding a spacer to corners of the dried indium tin oxide glass sample, heating the sample to a temperature above a glass transparent temperature, slowly pressing another indium tin oxide glass substrate on the sample, and then conducting cooling; and
   iv) enclosing the substrates using epoxy or a polyimide film, and then attaching an electrode thereto.

* * * * *